US009122178B2

(12) United States Patent
Ivanov et al.

(10) Patent No.: US 9,122,178 B2
(45) Date of Patent: Sep. 1, 2015

(54) OBJECT INSPECTION SYSTEMS AND METHODS

(75) Inventors: Vitalii Ivanov, Warsaw (PL); Vadim Yevgenyevich Banine, Deurne (NL); Arie Jeffrey Den Boef, Waalre (NL); Luigi Scaccabarozzi, Valkenswaard (NL); Nikolay Nikolaevich Iosad, Geldrop (NL)

(73) Assignee: ASML Netherlands B.V., Veldhoven (NL)

(*) Notice: Subject to any disclaimer, the term of this patent is extended or adjusted under 35 U.S.C. 154(b) by 212 days.

(21) Appl. No.: 13/388,267

(22) PCT Filed: Jul. 2, 2010

(86) PCT No.: PCT/EP2010/059460
§ 371 (c)(1),
(2), (4) Date: Jan. 31, 2012

(87) PCT Pub. No.: WO2011/015412
PCT Pub. Date: Feb. 10, 2011

(65) Prior Publication Data
US 2012/0127467 A1 May 24, 2012

Related U.S. Application Data

(60) Provisional application No. 61/231,161, filed on Aug. 4, 2009.

(51) Int. Cl.
*G01J 3/28* (2006.01)
*G01N 21/00* (2006.01)
(Continued)

(52) U.S. Cl.
CPC ............. *G03F 1/84* (2013.01); *G01N 21/6408* (2013.01); *G01N 21/6489* (2013.01);
(Continued)

(58) Field of Classification Search
CPC .......... G01N 21/6408; G01N 21/6489; G01N 21/65; G01N 21/94; G01N 21/9501; G01N 21/956; G03F 1/24; G03F 1/84; G03F 1/82; G03F 1/83
USPC .................................... 356/326, 237.2–237.6
See application file for complete search history.

(56) References Cited

U.S. PATENT DOCUMENTS 4,058,732 A * 11/1977 Wieder ...................... 250/461.1
4,127,318 A * 11/1978 Determann et al. .......... 359/387
(Continued)

FOREIGN PATENT DOCUMENTS

JP 63-103951 A 5/1988
JP 02-307047 A 12/1990
(Continued)

OTHER PUBLICATIONS

Westrate, S., et al., "Photoluminescence Mapping Detects CU Contamination in SI Wafers", Solid State Technology, vol. 45, No. 2, Feb. 1, 2002; 3 pages.
(Continued)

*Primary Examiner* — Michael A Lyons
*Assistant Examiner* — Shawn Decenzo
(74) *Attorney, Agent, or Firm* — Sterne, Kessler, Goldstein & Fox P.L.L.C.

(57) ABSTRACT

Methods and systems for inspection of an object include the use of spectroscopic techniques for the detection of unwanted particles on an object's surface, based on the different responses of the unwanted particles as compared with the object to be inspected due to their different materials. Time resolved spectroscopy and/or energy resolved spectroscopy of secondary photon emission from the surface of the object can be used to obtain Raman and photoluminescence spectra. The objects to be inspected can for example be a patterning device as used in a lithographic process, for example a reticle, in which case the presence of metal, metal oxide or organic particles can be detected, for example. The methods and apparatus are highly sensitive, for example, being able to detect small particles (sub 100 nm, particularly sub 50 nm) on the patterned side of an EUV reticle.

14 Claims, 18 Drawing Sheets

(51) Int. Cl.
*G03F 1/84* (2012.01)
*G01N 21/64* (2006.01)
*G01N 21/65* (2006.01)
*G01N 21/94* (2006.01)
*G01N 21/95* (2006.01)
*G01N 21/956* (2006.01)
*G03F 1/24* (2012.01)

(52) U.S. Cl.
CPC .............. *G01N 21/65* (2013.01); *G01N 21/94* (2013.01); *G01N 21/9501* (2013.01); *G01N 21/956* (2013.01); *G03F 1/24* (2013.01)

(56) References Cited

U.S. PATENT DOCUMENTS

| | | | |
|---|---|---|---|
| 5,046,847 A * | 9/1991 | Nakata et al. | 356/338 |
| 5,170,353 A * | 12/1992 | Verstraete | 701/423 |
| 5,293,210 A * | 3/1994 | Berndt | 356/39 |
| 5,298,963 A * | 3/1994 | Moriya et al. | 356/31 |
| 5,302,836 A * | 4/1994 | Siu | 250/559.34 |
| 5,768,434 A * | 6/1998 | Ran | 382/240 |
| 5,866,430 A * | 2/1999 | Grow | 506/6 |
| 6,045,502 A * | 4/2000 | Eppstein et al. | 600/306 |
| 6,081,119 A * | 6/2000 | Carson et al. | 324/307 |
| 6,274,874 B1 | 8/2001 | Sidhu | |
| 6,282,540 B1 * | 8/2001 | Goldensher et al. | 707/724 |
| 6,621,570 B1 * | 9/2003 | Danko | 356/237.4 |
| 6,740,890 B1 * | 5/2004 | Tai | 250/458.1 |
| 6,771,806 B1 * | 8/2004 | Satya et al. | 382/149 |
| 7,413,586 B2 * | 8/2008 | Ramamoorthy et al. | 55/385.1 |
| 7,433,033 B2 * | 10/2008 | Bleeker et al. | 356/237.2 |
| 7,433,034 B1 | 10/2008 | Huang | |
| 7,697,128 B2 * | 4/2010 | Snel et al. | 356/237.5 |
| 2001/0040722 A1 | 11/2001 | Shafer et al. | |
| 2002/0135759 A1 | 9/2002 | Ramamoorthy et al. | |
| 2006/0001877 A1 * | 1/2006 | Moriya | 356/369 |
| 2007/0070059 A1 * | 3/2007 | Rojer | 345/418 |
| 2007/0176119 A1 | 8/2007 | Hummel | |
| 2007/0258086 A1 | 11/2007 | Bleeker | |
| 2008/0084555 A1 | 4/2008 | Yoo | |
| 2008/0197277 A1 | 8/2008 | Nasser-Ghodsi et al. | |
| 2009/0009753 A1 | 1/2009 | Horai et al. | |

FOREIGN PATENT DOCUMENTS

| | | |
|---|---|---|
| JP | 06-036986 A | 2/1994 |
| JP | 09-210906 A | 8/1997 |
| JP | 11-304717 A | 11/1999 |
| JP | 2000-515641 A | 11/2000 |
| JP | 2005-215712 A | 8/2005 |
| JP | 2006-208210 A | 8/2006 |
| JP | 2007-258567 A | 10/2007 |
| JP | 2008-109012 A | 5/2008 |
| JP | 2009-002811 A | 1/2009 |
| WO | WO 98/11425 A1 | 3/1998 |
| WO | WO 02/29883 A1 | 4/2002 |
| WO | WO 02/077621 A1 | 10/2002 |
| WO | WO 2004/008125 A1 | 1/2004 |

OTHER PUBLICATIONS

International Search Report directed to related International Patent Application No. PCT/EP2010/059460, mailed Oct. 25, 2010, from the European Patent Office; 4 pages.

International Preliminary Report on Patentability with the Written Opinion of the International Searching Authority directed to related International Patent Application No. PCT/EP2010/059460, mailed Feb. 7, 2012, from the International Bureau of WIPO; 7 pages.

Scaccabarozzi, L., et al., "Cleaning and inspection of EUV reticles: specifications and prospects," Proceedings of the Eleventh International Symposium on Particles on Surfaces: Detection, Adhesion and Removal, 2008; 15 pages.

* cited by examiner

OBJECT INSPECTION SYSTEMS AND METHODS

CROSS-REFERENCE TO RELATED APPLICATIONS

This application claims the benefit of U.S. provisional application 61/231,161 which was filed on 4 Aug. 2009, and which is incorporated herein in its entirety by reference.

FIELD

Embodiments of the present invention generally relate to object inspection systems and methods, and in particular to object inspection systems and methods in the field of lithography, in which case the object to be inspected can for example be a reticle or other patterning device.

BACKGROUND

Lithography is widely recognized as one of the key steps in the manufacture of integrated circuits (ICs) and other devices and/or structures. However, as the dimensions of features made using lithography become smaller, lithography is becoming a more critical factor for enabling miniature IC or other devices and/or structures to be manufactured.

A lithographic apparatus is a machine that applies a desired pattern onto a substrate, usually onto a target portion of the substrate. A lithographic apparatus can be used, for example, in the manufacture of ICs. In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned.

Current lithography systems project mask pattern features that are extremely small. Dust or extraneous particulate matter appearing on the surface of the reticle can adversely affect the resulting product. Any particulate matter that deposits on the reticle before or during a lithographic process is likely to distort features in the pattern being projected onto a substrate. Therefore, the smaller the feature size, the smaller the size of particles critical to eliminate from the reticle.

A pellicle is often used with a reticle. A pellicle is a thin transparent layer that may be stretched over a frame above the surface of a reticle. Pellicles are used to block particles from reaching the patterned side of a reticle surface. Although particles on the pellicle surface are out of the focal plane and should not form an image on the wafer being exposed, it is still preferable to keep the pellicle surfaces as particle-free as possible.

A theoretical estimate of the limits of pattern printing can be given by the Rayleigh criterion for resolution as shown in equation (1):

$$CD = k_1 * \frac{\lambda}{NA_{PS}} \quad (1)$$

where $\lambda$ is the wavelength of the radiation used, $NA_{PS}$ is the numerical aperture of the projection system used to print the pattern, $k_1$ is a process dependent adjustment factor, also called the Rayleigh constant, and CD is the feature size (or critical dimension) of the printed feature. It follows from equation (1) that reduction of the minimum printable size of features can be obtained in three ways: by shortening the exposure wavelength $\lambda$, by increasing the numerical aperture $NA_{PS}$ or by decreasing the value of $k_1$.

In order to shorten the exposure wavelength and, thus, reduce the minimum printable size, it has been proposed to use an extreme ultraviolet (EUV) radiation source. EUV radiation sources are typically configured to output a radiation wavelengths of around 5-20 nm, for example, 13.5 nm or about 13 nm. Thus, EUV radiation sources may constitute a significant step toward achieving small features printing. Such radiation is termed extreme ultraviolet or soft x-ray, and possible sources include, for example, laser-produced plasma sources, discharge plasma sources, or synchrotron radiation from electron storage rings.

For certain types of lithography (e.g., most extreme ultraviolet (EUV) lithography processes), however, pellicles are not used. When reticles are not covered, they are prone to particle contamination, which may cause defects in a lithographic process. Particles on EUV reticles are one of the main sources, of imaging defects. An EUV reticle (or other reticle for which no pellicle is employed) is likely to be subjected to organic and inorganic particle contamination. Particle sizes as small as around 20 nm could lead to fatal defects on the wafer and to zero yield.

Inspection and cleaning of an EUV reticle before moving the reticle to an exposure position can be an important aspect of a reticle handling process. Reticles are typically cleaned when contamination is suspected, as a result of inspection, or on the basis of historical statistics.

Reticles are typically inspected with optical techniques. However, a pattern scatters light exactly in the same way as a particle does. The pattern of a reticle surface is arbitrary (i.e. non-periodic), and so there is no way to distinguish a particle from the pattern by simply analyzing the scattered light. A reference is always required with these optical techniques, either die-to-die, or die-to-database. Moreover, existing inspection tools are expensive and relatively slow.

It has been proposed to use the presence or absence of a photoluminescence (PL) signal as an indicator of the presence of a defect, see for example JP 2007/258567 or JP 11304717. However, improvements to the particle detection capabilities of these techniques would be welcomed.

SUMMARY

An object inspection system is provided that can operate at high speed and that can detect particles of small size, for example of a size of 100 nm or less, 50 nm or less, or 20 nm or less. A technique is also provided that can detect particles that are present on the patterned side of a patterning devices such as a reticle, used in a lithographic apparatus.

According to a first aspect of this disclosure, there is provided a method for inspection of an object including: illuminating the object with a radiation beam, analyzing secondary photon emissions from the object with time resolved spectroscopy, and determining that a particle is present if a time resolved spectroscopic signal is detected which is different from a signal that would be emitted by the object in the absence of a particle.

According to a second aspect of this disclosure, there is provided an apparatus for inspection of an object, including a radiation source arranged to emit a radiation beam onto the object and a spectrometer arranged to analyze secondary photon emissions from the object with time resolved spectroscopy and to determine that a particle is present if a time resolved spectroscopic signal is detected which is different from a signal that would be emitted by the object in the absence of a particle.

According to a third aspect of this disclosure there is provided a lithographic apparatus including an apparatus for inspection of an object which includes a radiation source arranged to emit a radiation beam onto the object and a spectrometer arranged to analyze secondary photon emissions from the object with time resolved spectroscopy and to determine that a particle is present if a time resolved spectroscopic signal is detected which is different from a signal that would be emitted by the object in the absence of a particle.

According to a fourth aspect of this disclosure there is provided a computer program product including instructions that, when executed upon a computer enable it to carry out a data analysis method for use in the method of the first aspect.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention. Embodiments of the invention are described, by way of example only, with reference to the accompanying drawings, in which.

Figure 1:
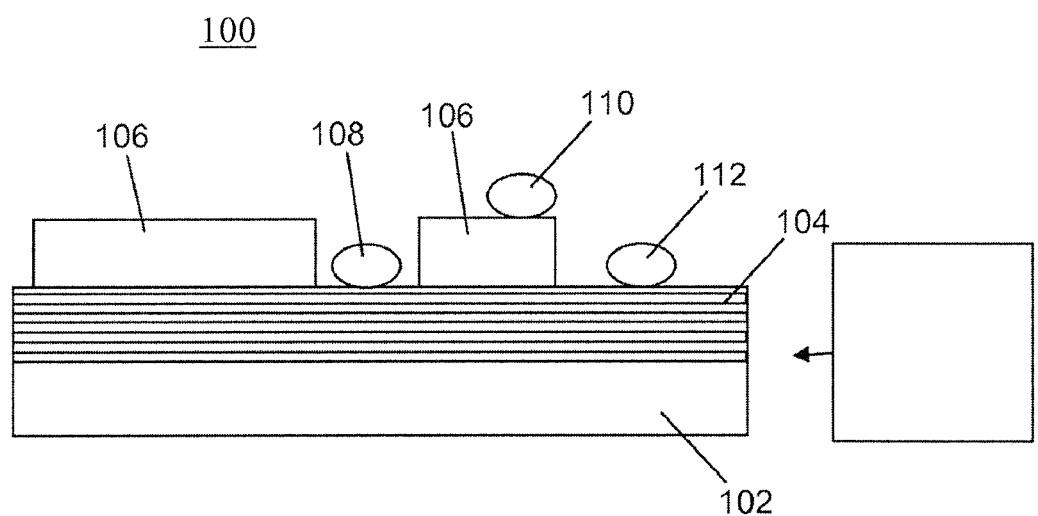
FIG. 1 depicts an EUV reticle with contaminant particles.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

Embodiments of the present invention are directed to object inspection systems and methods. This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention or of various component parts of the invention may be implemented in hardware, firmware, software, or any combination thereof. Embodiments of the invention of various component parts of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g.; carrier waves, infrared signals, digital signals, etc.), and others. Further, firmware, software, routines or instructions may be described herein as performing certain actions. However, it should be appreciated that such descriptions are merely for convenience and that such actions in fact result from computing devices, processors, controllers, or other devices executing the firmware, software, routines, instructions, etc.

The following description presents systems and methods of object inspection that allow the detection of particles on the object. The object to be inspected can be, for example, a lithographic patterning device for generating a circuit pattern to be formed on an individual layer in an integrated circuit. Example patterning devices include a mask, a reticle, or a dynamic patterning device. Reticles for which the system can be used include for example reticles with periodic patterns and reticles with non-periodic patterns. The reticles can also be for use within any lithography process, such as EUV lithography and imprint lithography for example.

FIG. 1 illustrates a typical EUV reticle 100 in cross section, including a substrate 102, multilayer coating 104 and pattern layer 106. The diagram also shows particles 108, 110 and 112. These are not part of the reticle 100 but may be adsorbed or deposited on the reticle 100 in some situations.

Because a lithography apparatus is complicated and utilizes many different materials, any type of particle can in principle be deposited on the reticle 100. The particles can be conductive or insulating, they can be of any shape or size and could be deposited on the conductive coating 104 or the pattern layer 106. Example types of particle that might be deposited include organic particles, metal particles and metal oxide particles.

In one example embodiment the reticle 100 can be a EUV reticle including a substrate 102 formed from quartz or another low thermal expansion material, and a reflective multilayer coating 104 including alternate molybdenum and silicon layers. The multilayer coating 104 may for example include a few tens of layers and can in one example have a thickness of about 200 nm. A capping layer (not illustrated) can also be provided at the top surface of the multilayer, being formed for example from ruthenium or silicon.

The pattern layer 106 defines a pattern for the reticle 100. In the case of an EUV reticle the pattern layer 106 is an absorber layer. Similarly, the multilayer 104 in an EUV reticle is reflective.

The pattern layer 106 in an EUV reticle can for example be formed from tantalum nitride (TaN) or TaNO. The height of the absorber may in one example be approximately 70 nanometers, and it can have a width of approximately 100 nm (which is approximately four times the critical dimension (CD) of the lithography system, the scaling being due to the demagnification factor between wafer and reticle).

The pattern defined by the pattern layer is in principle arbitrary and can be composed of lines, contact holes, periodic and non periodic patterns.

When electromagnetic radiation is incident on a surface of a solid, secondary radiation of photons occurs in addition to the regular reflection of the radiation. There are three main processes of secondary photon radiation on the surfaces of solids: photoluminescence (PL), inelastic light scattering processes (such as Raman scattering, and surface enhanced Raman scattering (SERS)), and elastic light scattering. The efficiency of each of these phenomena depends on the type of material involved.

Figure 2:
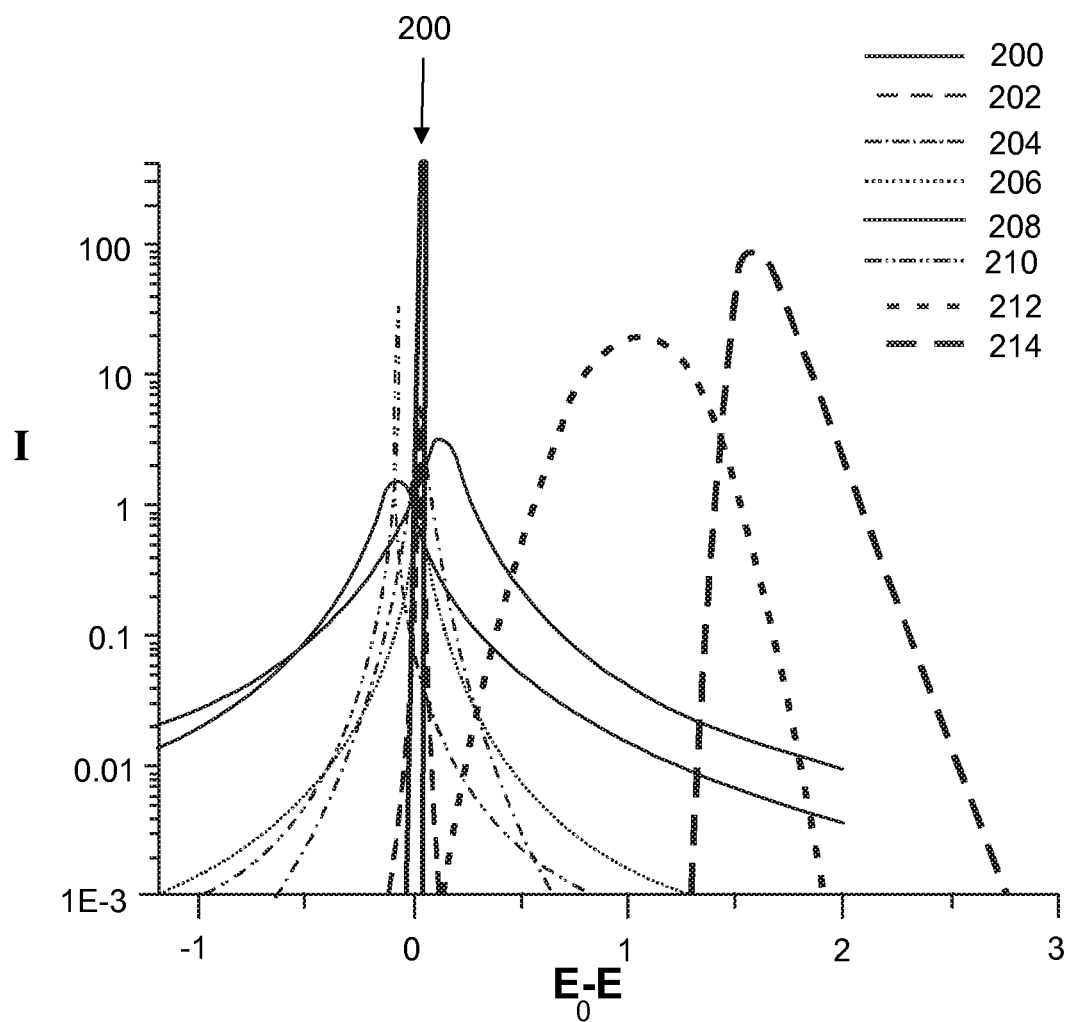
FIG. 2 depicts typical secondary emission spectra of various types of processes and particles.

Particles which gather on a surface of a patterning device such as a reticle used in a lithographic apparatus will in general be of a different type of material from those materials from which the patterning device is formed. The inventors have used Raman spectroscopy techniques to analyze the different responses of different materials. A typical secondary emission spectrum is shown in FIG. 2, which plots the intensity, I, in arbitrary units on the y-axis versus wavelength (shown here as an energy shift $E_0-E$) in arbitrary units on the x-axis. FIG. 2 illustrates the initial laser pulse 200 and the known Mie (202), Rayleigh (204) and Brillioun (206) scattering. In addition, FIG. 2 illustrates a typical Raman spectrum 208, the giant Raman spectrum 210 and photoluminescence spectra for a typical organic particle 212 and a typical metal oxide 214.

The main scattering signal from the pattern is the Mie (202), Rayleigh (204) and Brillioun (206) scattering at the same wavelength as laser, which is easily filtered out. Raman spectra from the absorber will actually be the "noise" in this approach. The signal from any particle will be given either by the giant Raman (210), organic photoluminescence (212) or metal oxide photoluminescence (214) spectra.

To further illustrate the industrial applicability of this technique, the photoluminescence of contaminations on silicon wafers was investigated.

Spectra of photoluminescence (PL) of samples of PSL (polystyrene latex), $Al_2O_3$ and $Fe_2O_3$ were studied at room temperatures. Samples were excited by emission of optical parametrical oscillator (OPO) in the spectral range 220-500 nm. Emission was analyzed and detected by optical spectrometer based on wide band single dispersion diffraction spectrograph/monochromator equipped with CCD image detector and time correlated single photon counting system. The spectral band of detection was limited in the range 200-1100 nm.

Three samples $Al_2O_3$ were prepared: a layer with a thickness of about 10 nm, a layer with a thickness of about 2 nm, and a sample with dots of $Al_2O_3$ deposited on a silicon wafer—the estimated density of dots was about $10^6$ $cm^{-1}$. The samples were subjected to excitation of 430 nm with power density 15 $kW/cm^2$ at room temperature.

Figure 3:
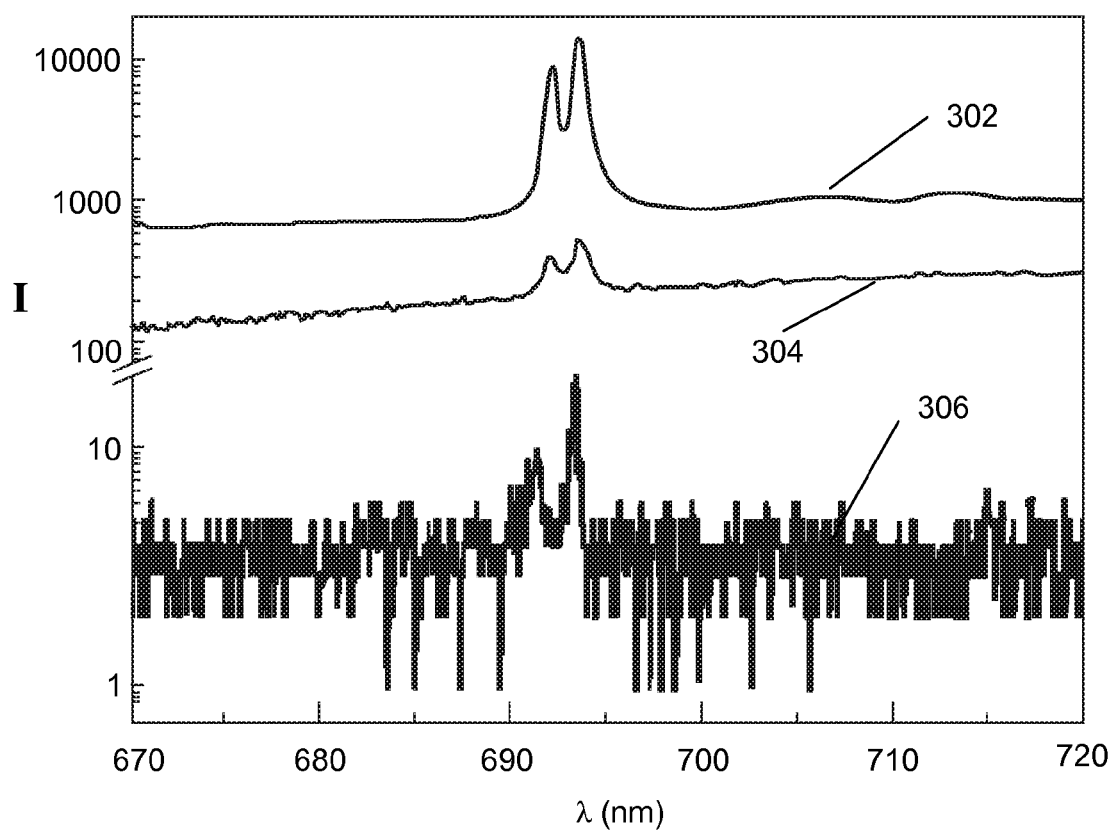
FIG. 3 depicts experimental results showing photoluminescence spectra of various $Al_2O_3$ samples on a silicon substrate.

FIG. 3 illustrates photoluminescence intensity, I, on the y-axis plotted against wavelength, $\lambda$, on the x-axis for each of the $Al_2O_3$ samples. Graph 302 illustrates the results for the 2 nm layer, graph 304 illustrates the results for the 10 nm layer, and graph 306 illustrates the results for the sample with dots of $Al_2O_3$ deposited on a silicon wafer. It can be seen from FIG. 3 that the samples of $Al_2O_3$ exhibit specific emission of $Cr^{3+}$ ions at 693 and 695 nm. The intensity of this emission is determined by a density of Cr ions contained in the $Al_2O_3$ as background impurities.

Figure 4:
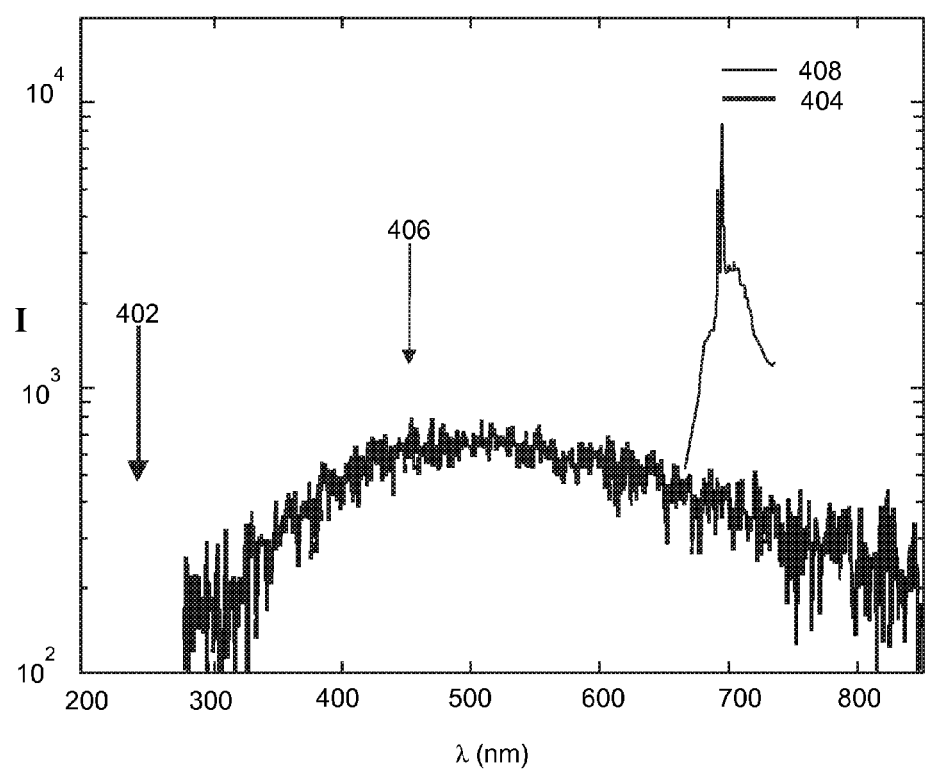
FIG. 4 depicts experimental results showing a photoluminescence spectrum from a polystyrene latex sample and an $Al_2O_3$ sample.

In a second experiment, emission from a PSL sample was detected at wide spectral band under UV excitation 223 nm. The sample was exposed for 0.2 seconds with power density 52 $kW/cm^2$. The results are shown in FIG. 4, which plots photoluminescence intensity, I, in arbitrary units on the logarithmic y-axis versus wavelength, $\lambda$, on the x-axis. The laser excitation wavelength for PSL 402 is shown and graph 404 represents the results for the photoluminescence of the PL sample.

The results of a further experiment are also shown on FIG. 4. The laser excitation wavelength for $Al_2O_3$ 406 is shown and graph 408 represents the results for the photoluminescence of the $Al_2O_3$ sample. Data is not comparable between graphs on the intensity axis.

Figure 5:
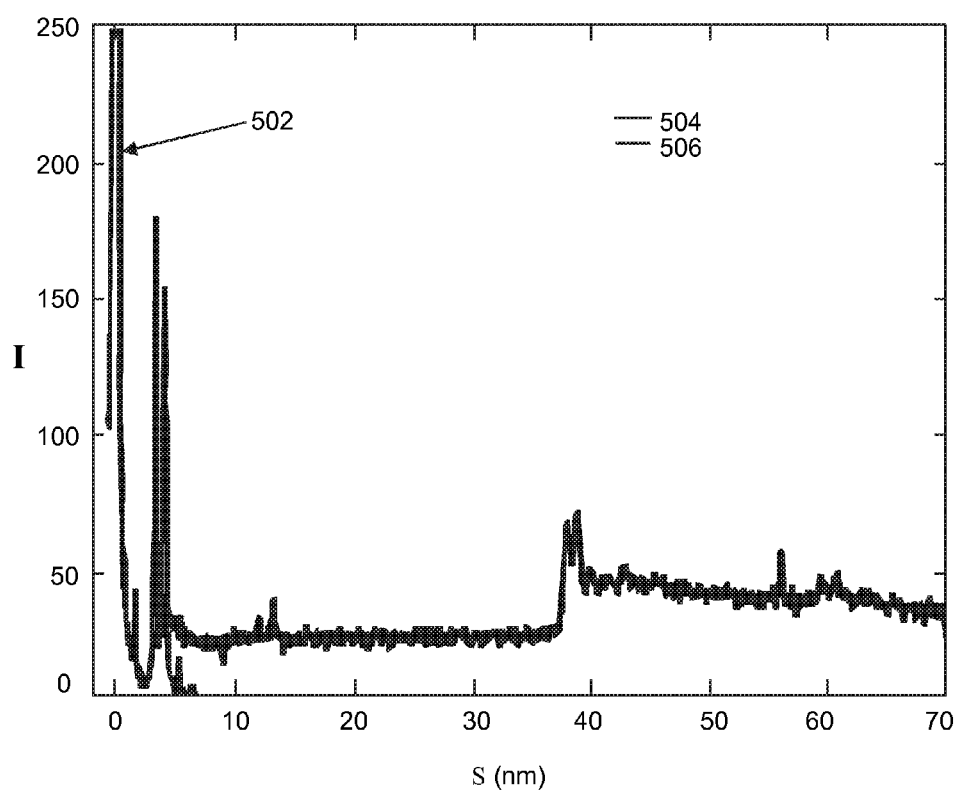
FIG. 5 depicts experimental results showing a laser line, Raman shift for an $Al_2O_3$ sample and surface enhanced Raman scattering (SERS) from a metal surface.

The results of a further Raman shift experiment are shown in FIG. 5, which plots photoluminescence intensity, I, in counts per second on the y-axis versus Raman shift, R, in nanometers on the x-axis. The excitation laser line 502 is shown and graph 504 represents the Raman shift results for the $Al_2O_3$ sample. Graph 506 represents the surface enhanced Raman scattering (SERS) results from a metal surface.

Figure 6:
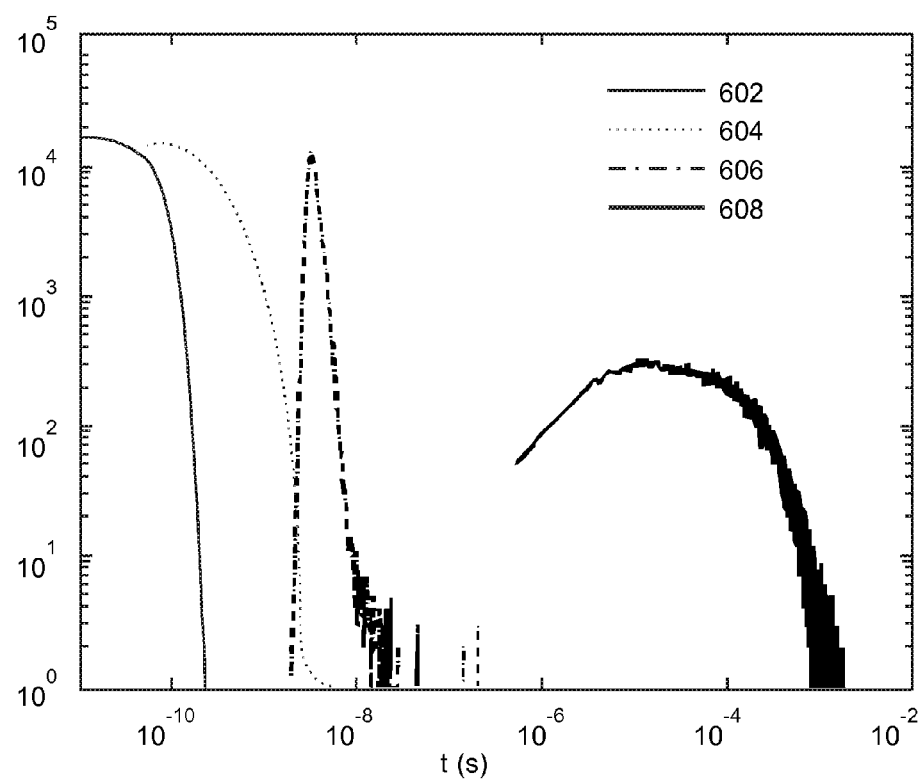
FIG. 6 depicts experimental results showing time domain response of a polystyrene latex sample and an $Al_2O_3$ sample.

The results of further time domain experiments are shown in FIG. 6, which plots photoluminescence intensity, I, in arbitrary units on the logarithmic y-axis versus time, t, in seconds on the logarithmic x-axis. The excitation laser response 602 is shown at the left and graph 604 represents the scattering response. Graph 606 represents the results for the photoluminescence of the PL sample in the time domain. Graph 608 represents the results for the photoluminescence of the $Al_2O_3$ sample in the time domain. Data is not comparable between graphs on the intensity axis.

In the method a short laser pulse, for example a picosecond laser pulse, at a predetermined wavelength, for example an ultraviolet wavelength, is used as a probe. The scattered and emitted light are collected and analyzed as will be discussed below. The major signal from the pattern is equivalent to scattered light at the same wavelength of the probe and can be easily filtered out.

By looking at wavelengths neighboring the wavelength of the probe laser pulse, the Raman spectrum can be recorded and by looking at a broader range of wavelengths, the photoluminescence of the surface can be recorded.

If a particle is present, a spectrum of secondary emission will be emitted that will be different from that of the surface of the object in either or both of the photoluminescence or the Raman spectra, provided that the material of the particle is different from that of the object to be inspected. The different spectroscopic response provides the basis for determining the presence of a particle.

The presence of an unexpected or different spectroscopic response in itself can be used as a test to determine the absence/presence of a particle. This is the primary concern in passing an object as free from particle contamination. However, in alternative embodiments, further information about the spectra obtained can be used to characterize at least the type of the particle, or even the specific material or materials from which the particle is formed.

Therefore, it can be seen that spectroscopic analysis in the energy domain can be used for the detection of particles on a reticle surface.

It is also possible to perform time resolved spectroscopy of secondary photon emission from the surface of an object for the detection of particles, the term "time resolved spectroscopy" referring in general to analysis of a signal in the time domain, and alternatively referred to as "time resolved measurement". The object can be a patterning device used in a lithographic apparatus, such as a reticle for example. Time resolved spectroscopy can be used as an alternative to energy resolved spectroscopy, or the two techniques can be used in combination, being performed either simultaneously or sequentially in any order.

Scattered and emitted light can be collected and analyzed in the time domain. Time resolved measurement is possible for both the Raman and the photoluminescence spectra. In the case of the Raman spectra the time resolution is typically very fast—in the order of picoseconds. The process of photoluminescence can take place on similar short timescales, or can occur over a much longer period of time, microseconds or milliseconds.

A particle will exhibit a certain response in the time domain which is different from the response of a particle-free area of the object. Organic particles, for example, are characterized by a long timescale photoluminescence emission (in the order of milliseconds). Metal oxides are characterized by strong lines in the photoluminescence spectrum (the measured signal being derived from impurities inside the metal oxides, for example $Cr_3^+$ ions in $Al_2O_3$) and microsecond scale photoluminescence emissions, while the time varying emissions from a metal particle can be detected by fine resolved time resolution techniques.

The energy domain spectrum shown in FIG. 2 will also differ in time.

Either or both of the energy resolved and time resolved spectroscopic methods can be optionally further enhanced by the use of noise reduction techniques.

In a first example, the noise reduction techniques may include cross-correlation or autocorrelation techniques.

These techniques are used to discriminate the wanted signal from a noisy background, and can be advantageous because of the complicated photonic response exhibited by a reticle because of the various materials which are found in it.

A correlation function $G(\tau)$ is defined as follows:

$$G(\tau) = \lim_{T \to \infty} \int_{-T}^{T} I(t) J(t+\tau) dt \qquad (2)$$

In this equation, I(t) and J(t) are signals which depend upon time. $G(\tau)$ is referred to as an auto-correlation function if I(t) and J(t) are the same signals, and is referred to as a cross-correlation function if I(t) and J(t) are different signals.

A digital correlator provides a good approximation to the true correlation function whenever a change in a value of the correlation function during a time period $\Delta t$ of sampled time periods is small. The digital correlation function is given by:

$$G(k\Delta\tau) = \sum_{i=0}^{N-1} n_k \tilde{n}_{i+k} \qquad (3)$$

In equation 3, $G(k\Delta\tau)$ represents the correlation function of the $k^{th}$ channel, while $n_k$ represents the number of times the content of each stage of a shift register is added to its respective correlation function memory channel, and the numbers $\tilde{n}_{i+k}$ are the numbers stored in the shift register.

Cross-correlation is used in embodiments of the present system to filter out unwanted effects like variations in laser stability.

In general, autocorrelation of a broadband signal is a simple Fourier transform of the power spectrum of the signal. However, in the present disclosure autocorrelation allows the separation of processes related to the reflection of light that are Markovian from those which are from scattered light which are non-Markovian.

In a second example noise reduction technique, a tool kit developed by chaos theory can be used. This technique can be used to discriminate the wanted signal from a noisy background, and can be advantageous because of the complicated photonic response exhibited by a reticle because of the various materials which are found in it.

A sensor, such as a CCD, produces a frequency resolved spatial image of the reticle when moved over the surface of the reticle. Based on empirically collected data about characteristic photonic signatures of possible contaminants, a correlator can perform reselection of data in frequency and time intervals of interest. Wavelet analysis can then be performed on the data, which then enables principles of chaos theory to be used to reconstruct attractors. These obtained attractors can then be compared with a library of attractors associated with contaminants. In the case of correspondence or close resemblance, the reticle is considered to be contaminated.

This approach can function because both Raman emission and PL are non-Markovian processes with well pronounced memory, namely, these processes have strong dependence on the prehistory of the light emitting object.

Figure 7:
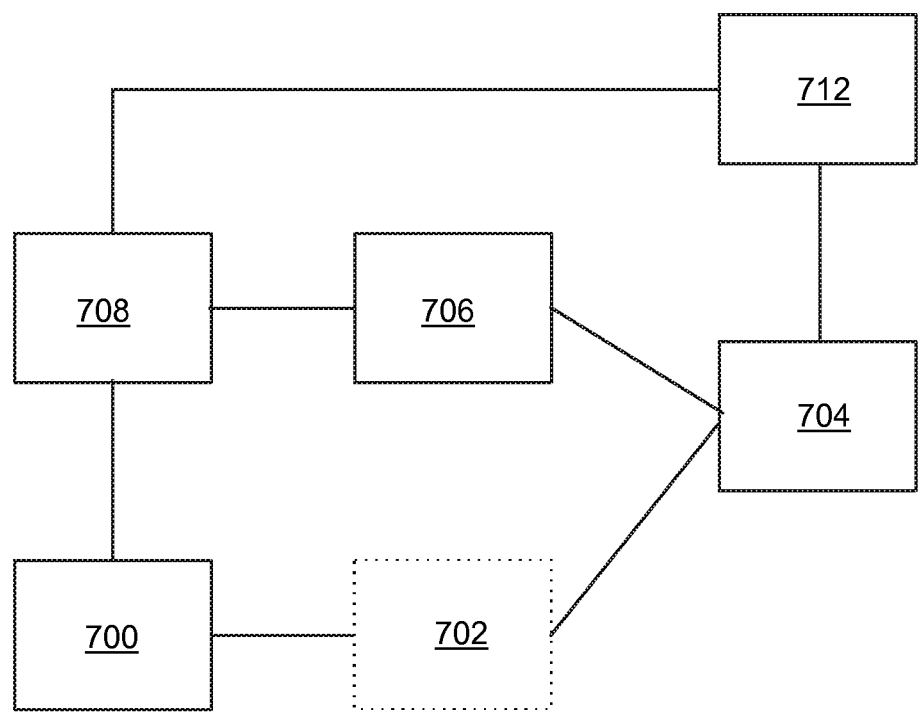
FIG. 7 depicts a generic apparatus for inspection of an object according to an embodiment of the present invention.

FIG. 7 shows an exemplary apparatus for performing the methods described above, namely either energy resolved spectroscopy, time resolved spectroscopy or both. It is to be appreciated that this specific set-up is given as an example to better understand the principle of operation of the invention and it will be appreciated that the person skilled in the art will be able to envisage many alternative arrangements that may perform similar functions.

In FIG. 7 a laser source 700 is provided, which can optionally be operated together with a tuner 702 which can be used to select the best wavelength for the probe beam. The laser probe beam is then incident on the sample stage 704 which holds the object to be inspected. Light reflected and/or scattered from the sample stage 704 passes through an optical system 706 and is then processed by spectrometer module 708 which may include a radiation detector which can be a charge-coupled device (CCD), for example a gated CCD.

In one embodiment the optical system 706 can include a beam splitter and other optical elements that split the beam from the sample 704 into two optical paths, or branches. The spectrometer module 708 then includes a first spectrometer for analyzing a first branch, and a second spectrometer for analyzing the second branch, and a correlator for performing a correlation between the two branches, as will be described in more detail below.

Alternatively, a single branch can be analyzed by a single spectrometer in a spectrometer module 708, or more than two branches could be provided for additional analyses.

The output of the laser source 700 is also fed to the spectrometer module 708 as a time reference signal. The data from the spectrometer module 708 (or, from the corresponding radiation detector) is fed to computer 712.

Computer 712 may be in communication with the sample stage 704 to perform functions, for example moving the sample stage and so on.

The connections between the various components in FIG. 7 may represent optical paths or logical links or data links as appropriate.

Furthermore, a correlator can be added to the system for performing autocorrelation or cross-correlation. In the example of FIG. 7 (together with FIGS. 8 and 9, to be discussed below), the inputs to the correlator may for example include a slave and a master gated CCD, each of them being equipped with a monochromator in order to perform spectral pre-selection of signals. The cross-correlator may start collecting a signal on the slave CCD after a certain signal is collected from the master CCD.

As discussed above, FIG. 7 is a schematic illustration only. The figure shows radiation being incident upon a sample stage 704 at an angle, however it will be appreciated that this is for the ease of illustration only. In some embodiments the incident radiation will indeed be incident at an angle. However, in alternative embodiments, the radiation can be incident on the sample stage 704 at a normal incidence. This type of arrangement is particularly suited for the detection of particles in trenches that exist in the surface of the object under inspection.

Figure 8:
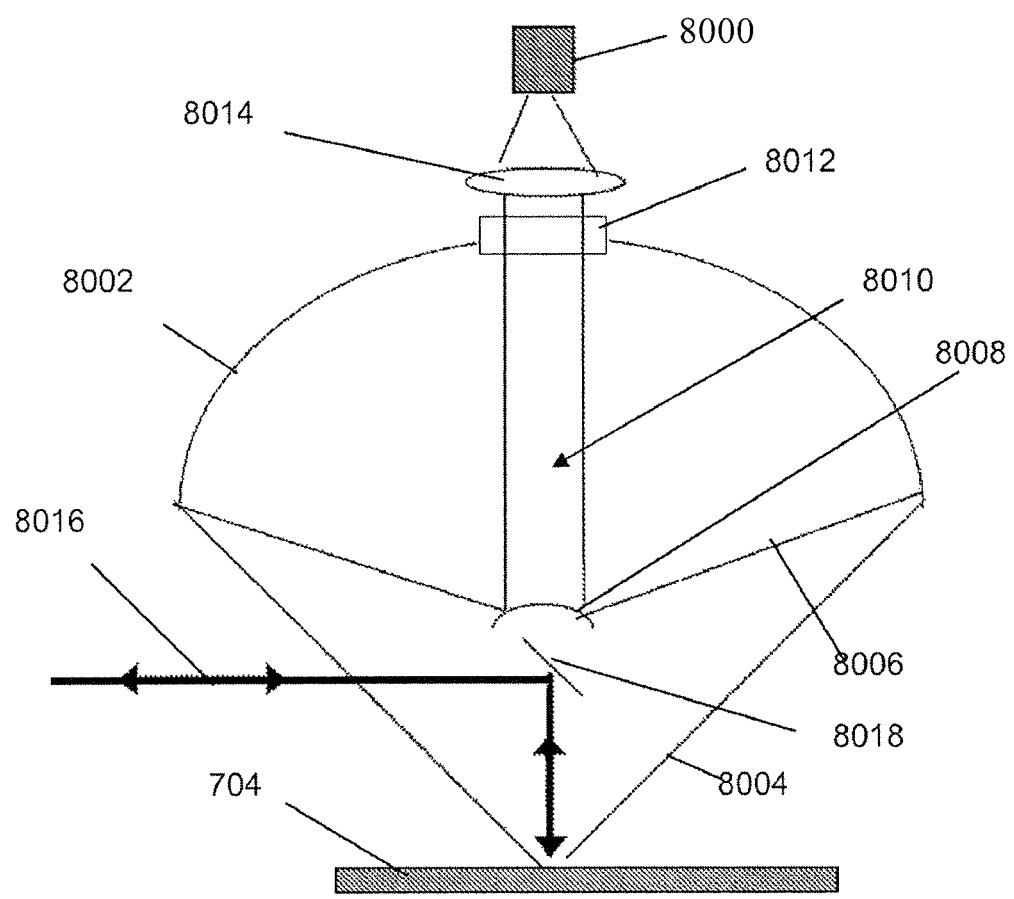
FIG. 8 depicts an arrangement for normal incidence inspection of an object.

FIG. 8 shows an example arrangement for normal incidence inspection of a sample stage 704, by a detector 8000 which may form part of the spectrometer/detector unit 708. The optical system (shown generally as 706 in FIG. 7) in this example comprises a Schwarzschild type collector comprising a first mirrored surface 8002 that gathers scattered radiation 8004 and reflect the scattered radiation 8006 towards a second reflective surface 8008, the shape of which is designed, in cooperation with the first reflective surface 8002 to form a collimated beam 8010 of radiation, which passes through aperture 8012 and objective optics 8014, focusing the beam 8010 onto the detector 8000. An additional intermediate focus is also possible for filtering or for an additional aperture. The scattered radiation 8004 is that scattered from a probe beam 8016 which is normally incident on the surface 704, for example by reflecting it from a reflective surface 8018.

It will be appreciated that other types of collector optics might be used, as appropriate.

In the embodiment shown in FIG. 8, and in its equivalents, the signal path is free from beamsplitters, which maximizes the amount of collected signal.

In an alternative embodiment, an off-axis illumination from a more than one direction can be employed. Several mask inspection techniques use a dark field-type of illumination where the laser or other light source is incident at an angle to the surface. This is done to avoid collecting the zero-th order (reflected) beam. Such an approach works in general quite well, but there is a problem if the particle size that needs to be detected is of a comparable magnitude to, or less than, the height of features that form part of a surface pattern, an example being detection of particles on EUV reticles, where the particle size to detect can be around 20 nm and the absorber pattern height can be around 70 nm. This produces a shadowing effect, which is illustrated in FIG. 9a. As can be seen here, some of the incident illumination 970 is blocked from reaching a particle 972 because of a feature 974 of the pattern on the surface. This creates a shadowing effect, illustrated at 976, that is, a region is created that will not be illuminated by incident illumination. This region 976 may be large enough for an entire particle to be effectively completely hidden from view, or at least partially obscured, leading to a drop in signal intensity that can be detected from that particle and an increased risk of not detecting it.

A solution to this problem is shown in FIG. 9b. Here, illumination from a single direction is replaced by illumination 978, 980 from two directions. It can be seen that the particle 972 can now be detected, as illumination 980 from the second direction is not blocked by the feature 974 from being incident on the particle 972.

Figure 9:
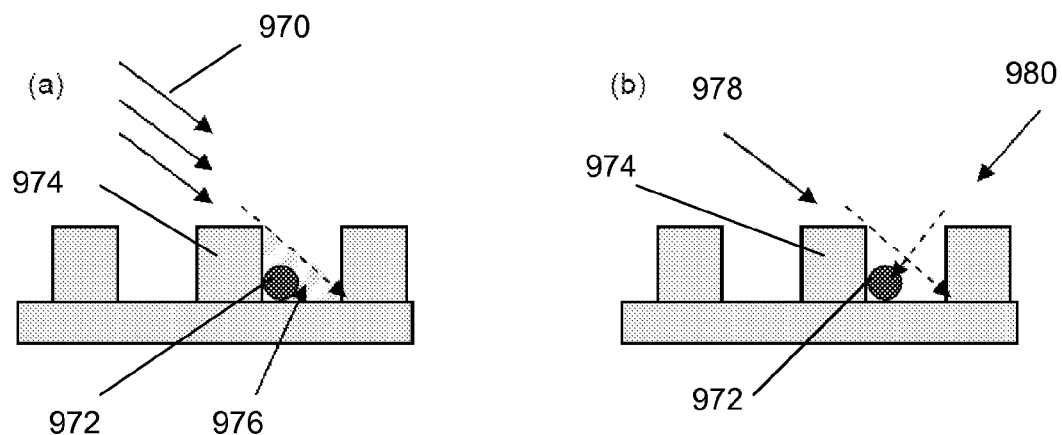
FIG. 9 depicts a shadowing effect, and its solution using illumination from two different directions.
Figure 10:
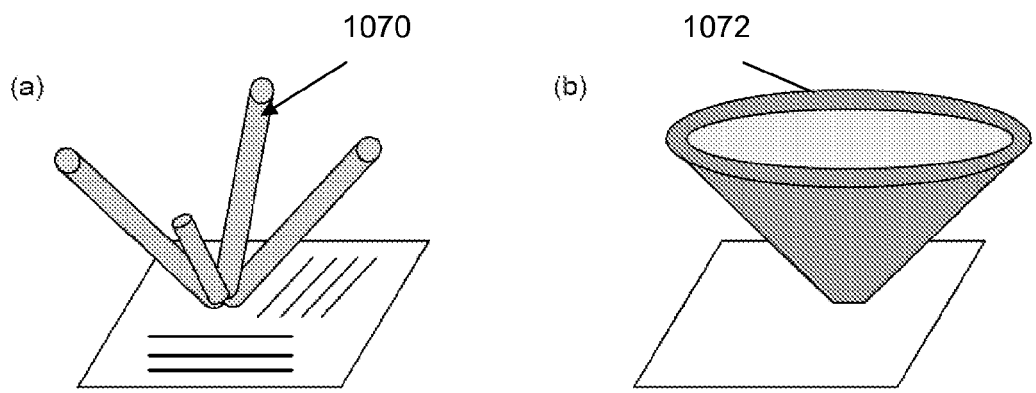
FIG. 10 depicts illumination of an object from four different directions and with an annular beam.

FIG. 10a shows the extension of the illustration of FIG. 9 to three dimensions. Because patterns are in principle arbitrary, vertical and horizontal lines may be present on the same object. For this reason it is advantageous to provide illumination 1070 from at least four directions, as shown in FIG. 10a. Even better performance may be obtained by using an annular type of illumination 1072, as shown in FIG. 10b.

An off-axis illumination from a more than one direction can be obtained either by splitting the beam using beam splitters and redirecting the resulting beams (using mirrors) to the same spot from different directions or by using a darkfield type of illumination (i.e., by using a central obscuration in the pupil plane or by using, e.g., diffractive optical elements).

Figure 11:
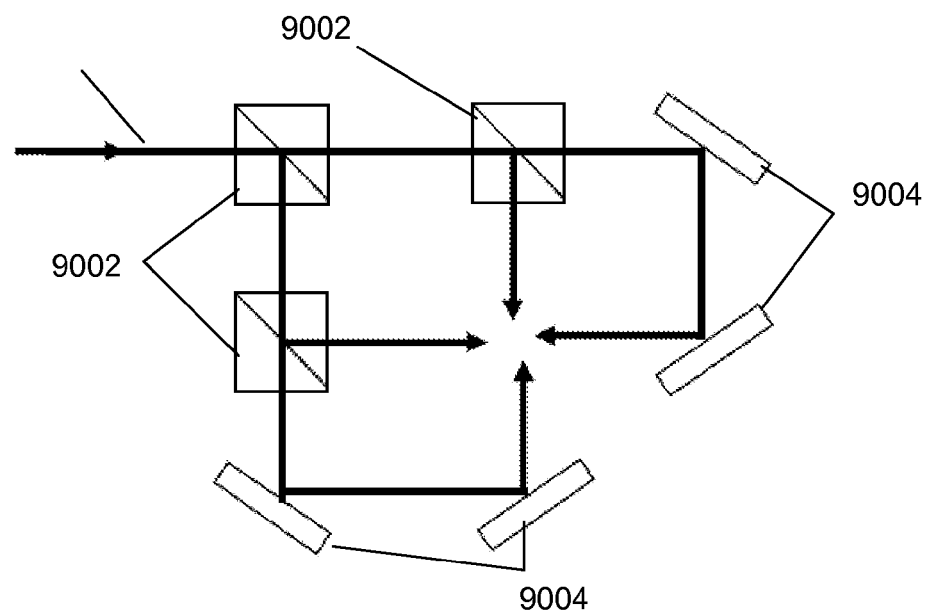
FIG. 11 depicts a "multibeam" configuration, in which radiation is incident on an object at multiple angles.

An example such configuration is shown in FIG. 11, in which a probe beam can be split so that radiation can be incident on a sample stage 704 at multiple angles. This embodiment is also useful for detecting of particles in trenches that exist in the surface of the object under inspection. The signals from different angles can then be compared, to verify detection results and to identify particles that are detected from one angle but not another.

In the example arrangement of FIG. 11, a probe beam 9000 is processed by beamsplitters 9002 and reflective surfaces 9004 in an arrangement that produces four split beams incident on a detection point at four different directions.

It will be appreciated that other arrangements of beamsplitters, reflective surfaces or other optical components may be employed to achieve similar results, and that the number of different angles of radiation does not have to be four, it can be anything from two upwards. Also, the different angles of radiation do not need to be perpendicular, the illustration is only one special case.

Figure 12:
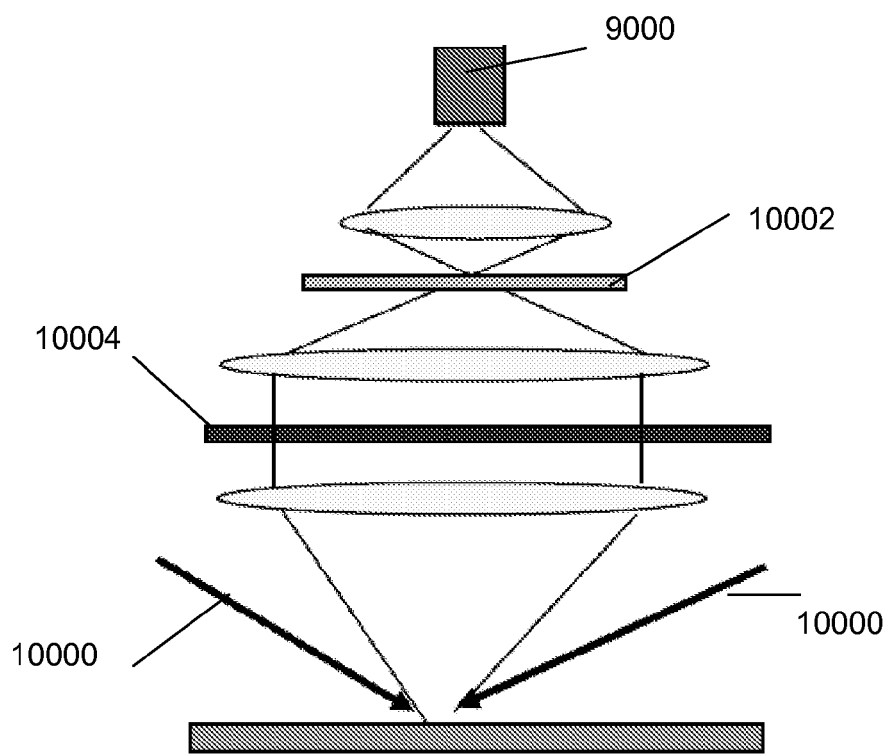
FIG. 12 illustrates optical elements for use with the multibeam configuration of FIG. 11.

FIG. 12 shows one example of optical elements that may be employed for detection of radiation from a multibeam configuration, such as that shown in FIG. 11, or that may form part of the objective optics shown generally at 8014 in FIG. 8. Incident radiation 10000 passes through a filter 10002 and aperture 10004, with interposed lenses as illustrated. The radiation is focused on detector 9000.

The inspection methods and apparatus of the present disclosure involve directing the radiation to illuminate a given area of an object under test. A scanning process is then carried out to cover the entire object. In a preferred embodiment, the object under test will not have any significant spectral response in the observed energy range. This is the case, for example, when a lithographic reticle is inspected by a UV laser. The signal (and therefore signal-to-noise ratio) of the particle is essentially independent of the collection area. For this reason, the larger the collection area, the smaller the total inspection time. However, the location accuracy also decreases with a larger the area.

In order to increase the accuracy of detection without unreasonably increasing the inspection time, it is possible to adopt a scanning strategy as follows. Firstly, a first area of the object is scanned. If one or more particles are detected, that first area is then segmented into two or more portions. Those portions are then separately scanned, and the presence of a particle can be detected in each of the segmented portions. The detection process can either stop there, or a further segmentation and scanning process can be performed. This can be repeated as often as desired, to obtain particle detection to a predetermined accuracy.

Figure 13:
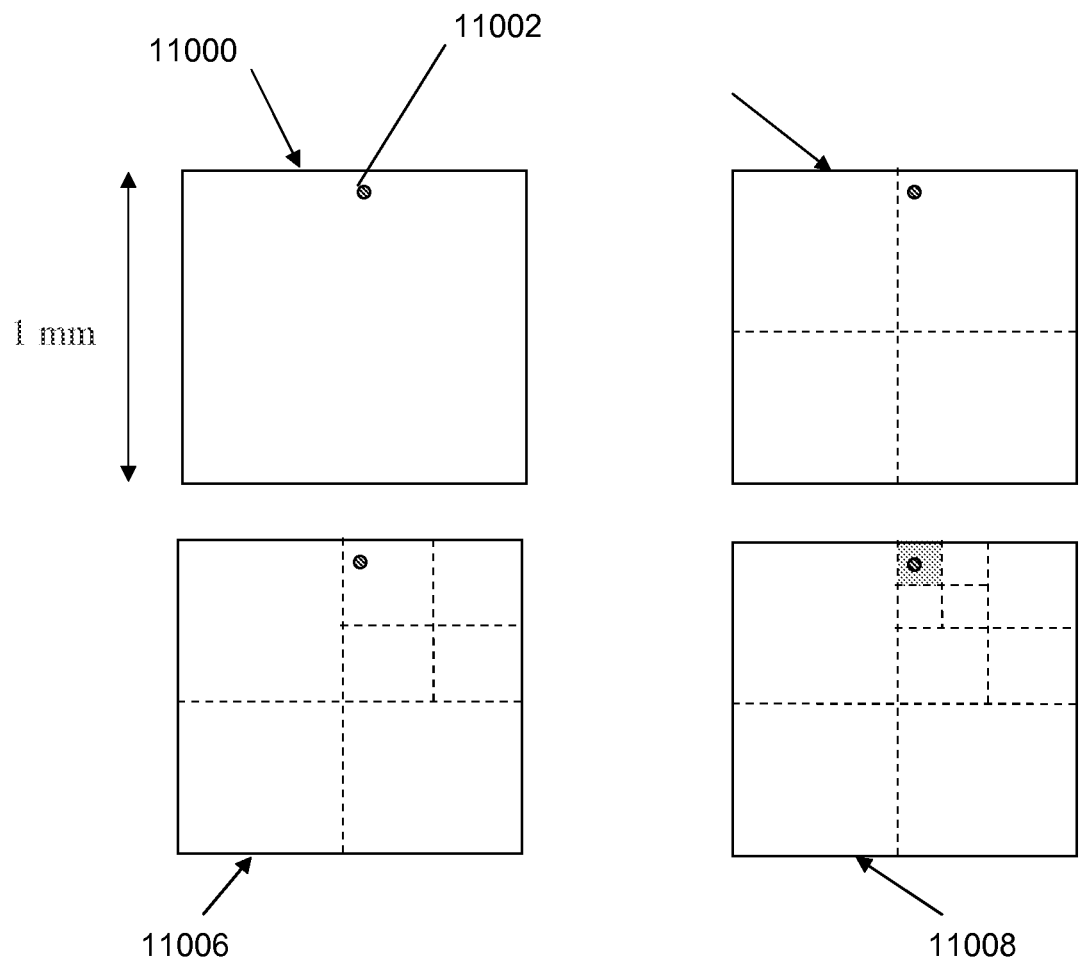
FIG. 13 illustrates a method of subsampling an area, to improve positional accuracy of defect detection.

FIG. 13 shows the operation of this scanning strategy, for the case of a single particle being present in the area of a first scan. This first scan 11000 may for example be performed over an area that is 1 mm square, and may comprise a particle 11002. The first scan will give a result that indicates the presence of a particle. However, no information is given on the position of that particle within the area of the first scan 11000. Because a detection result is achieved, a second scan 11004 is carried out. The area of the first scan 11000 is split into four quadrants, each of which is scanned individually. In this example, the top-right quadrant gives a positive detection result. That quadrant can then be segmented into four further sub-quadrants in a third scan 110006. In this example, the top-left quadrant now gives a positive detection result. That quadrant can then be segmented into four further sub-quadrants in a fourth scan 110008.

After the fourth scan as illustrated in FIG. 13, the position of the defect 11102 is found to within an accuracy of ⅛ square millimeters. Further iterations can be performed to obtain the position of the defect to greater accuracy. Alternatively, the detection could stop after a single segmentation has been performed.

It will also be appreciated that other segmentations could be used, other than quarters. For example, the area scanned could be split into halves, ninths, sixteenths, or any other arbitrary number of segments with each iteration.

The re-scanning of segments may be accomplished by putting an aperture in the collection optics, which decreases the collection area (by an appropriate factor—four in the example of FIG. 13) and by positioning the reticle appropriately.

If more than one particle is present in the initial scan, then each quadrant that subsequently yields a detection result needs to be segmented and scanned, until the required resolution limit has been reached.

With such a process it is possible to locate a particle to within an arbitrary accuracy, limited only by physical constraints of the measurement system, such as stage accuracy, and the minimum aperture size that can be achieved. As for the throughput, we can calculate how many iterations are necessary to locate a particle with a certain accuracy, say 200 nm, for an initial scan area of 1 mm: 1 mm/2N=200 nm; N=(1/l n2)·ln(1 mm/200 nm)~13. That is, thirteen additional iterations (or 13×4=52 acquisitions) are necessary to reach the desired accuracy of 200 nm. If we assume an acquisition time of ~1 s, this means that for each particle, we need one additional extra minute to reach the wanted accuracy. The estimated inspection time (for 1 mm accuracy, 20 nm particle size) is of about 30 min. So, the total inspection time will be ~30 min+1 min/particle.

This approach would only work for relatively small numbers of particles, probably only being viable for around ten particles or so per reticle. However, the number of particles will in practice be around this range or less. If ten or more particles are present on a reticle, that usually means that there is a major fault elsewhere in the lithographic apparatus and the reticle must be cleaned.

Figure 14:
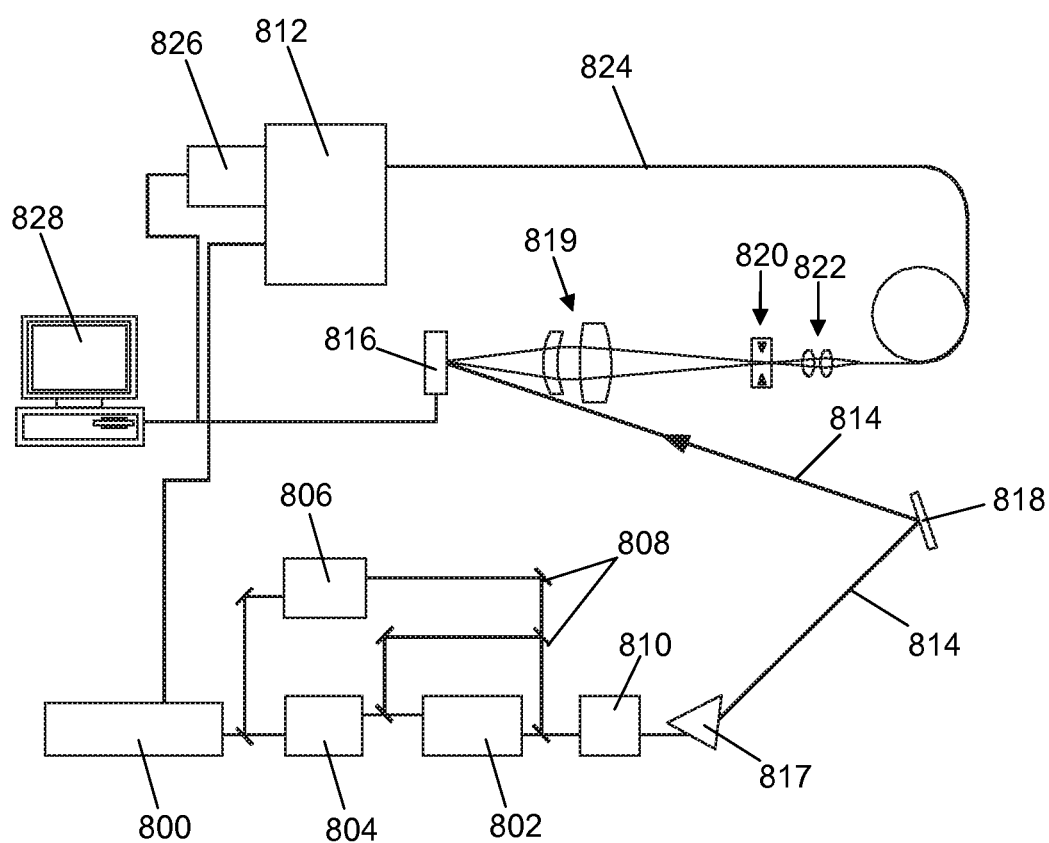
FIG. 14 depicts a first example of an apparatus for inspection of an object according to an embodiment of the present invention.

FIG. 14 illustrates a first example set up, again for the purposes of illustration. Laser source 800 is provided which can in the example be a Nd:YAG laser together with a second harmonic generator. It will be appreciated that any other type of pulsed laser may be used. A laser tuner includes an optical parametric oscillator 802 together with third and fourth harmonic generators 804, 806; various reflective elements 808 which may, for example, be reflective surfaces such as mirrors or beam splitters, and attenuator 810.

The output from the laser 800 is fed to a spectrometer 812 as a reference signal. Meanwhile the tuned output from the laser and tuner forms a probe beam 814 which is directed towards a sample stage 816 which carries an object to be inspected. For example, the sample stage may be a reticle stage holding a reticle for inspection. In the illustrated optical path a prism 817 and reflective element 818 are shown; however, it will be appreciated that any suitable components may be used to direct the probe beam 814 in a known manner in any particular arrangement according to the physical layout of the components.

The reflected probe beam 814 then passes through an optical system including a condenser 819, pin hole filter 820 and collimator 822 being fed into a fiber optical cable 824 for input into the spectrometer 812. The spectrometer operates in conjunction with a sensor 826, which in this example may be a gated CCD.

The output of the sensor 826 is fed to computer 828 for data analysis. The computer 828 is also in communication with the sample stage 816 for movement and so on.

Analysis of the signal in the energy and time domain can be carried out by the spectrometer which may include a monochromator and a CCD, and, for example, by a time correlated detection system, for example a single-photon counting detection system.

Figure 15:
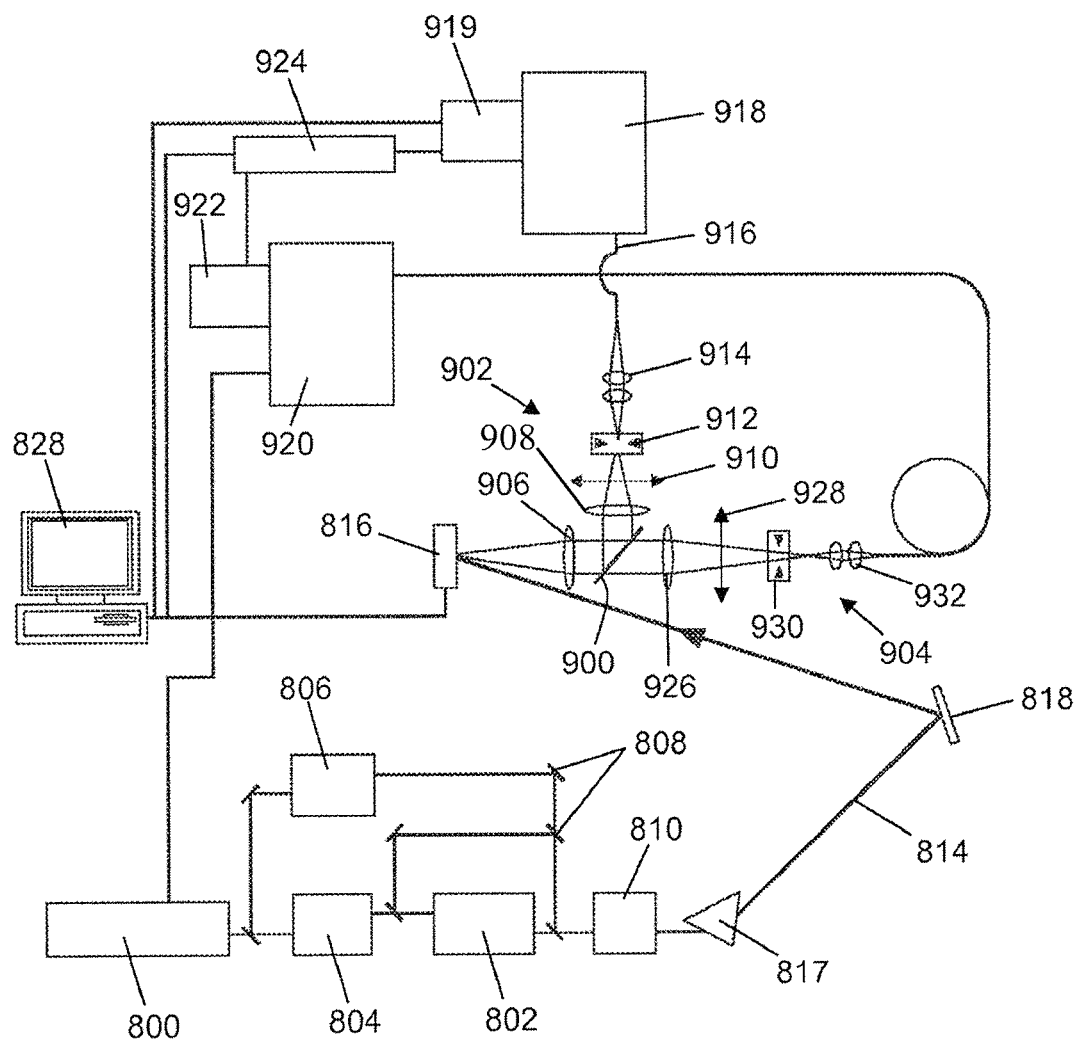
FIG. 15 depicts a second example of an apparatus for inspection of an object according to an embodiment of the present invention.

FIG. 15 illustrates a second example set-up, again for the purposes of illustration. This is a variation of the set-up shown in FIG. 14. Similar elements are illustrated with similar reference numerals and function in the same manner as mentioned above. They will therefore not be described again in detail.

In the example set-up of FIG. 15, the optical system (shown in general as reference numeral 706 in FIG. 7) includes a beam splitter 900 that splits the beam reflected from the sample stage 816 into a first optical path, or branch, 902 and a second optical path, or branch, 904. Data from the first branch 902 is analyzed by a first spectrometer 918 which operates in conjunction with a sensor 919, and data from the second branch 904 is analyzed by a second spectrometer 920 which operates in conjunction with a sensor 922. The sensors 919, 922 may in this example be gated CCDs. The outputs from each of the sensors 919, 922 are input to a correlator 924 for comparison, as will be described below. The two spectrometers 918, 920 together with the correlator 924 together include a "spectrometer module" of the type shown in FIG. 7. The term "spectrometer module" can alternatively refer to the spectrometers themselves, with the correlator 924 being provided as a separate unit. The two spectrometers 918, 920 and/or the correlator 924 may be provided within the same housing or within separate housings, as appropriate.

The correlator 924 functions to discriminate the wanted signal from a noisy background, as described above.

The beam reflected from the sample stage 816 is focused onto beam splitter 900 by lens element 906. The first branch 902 includes a lens element 908, polarizer 910, pin hole filter 912 and collimator 914, so that the data is fed into a fiber optical cable 916 for input to the first spectrometer 918; while the second branch 904 includes a lens element 926, polarizer 928, pin hole filter 930 and collimator 932, so that the data is fed into a fiber optical cable 934 for input to the second spectrometer 920.

The output of the spectrometers 918, 920 and from the correlator 924 are fed to computer 828 for data analysis.

Figure 16:
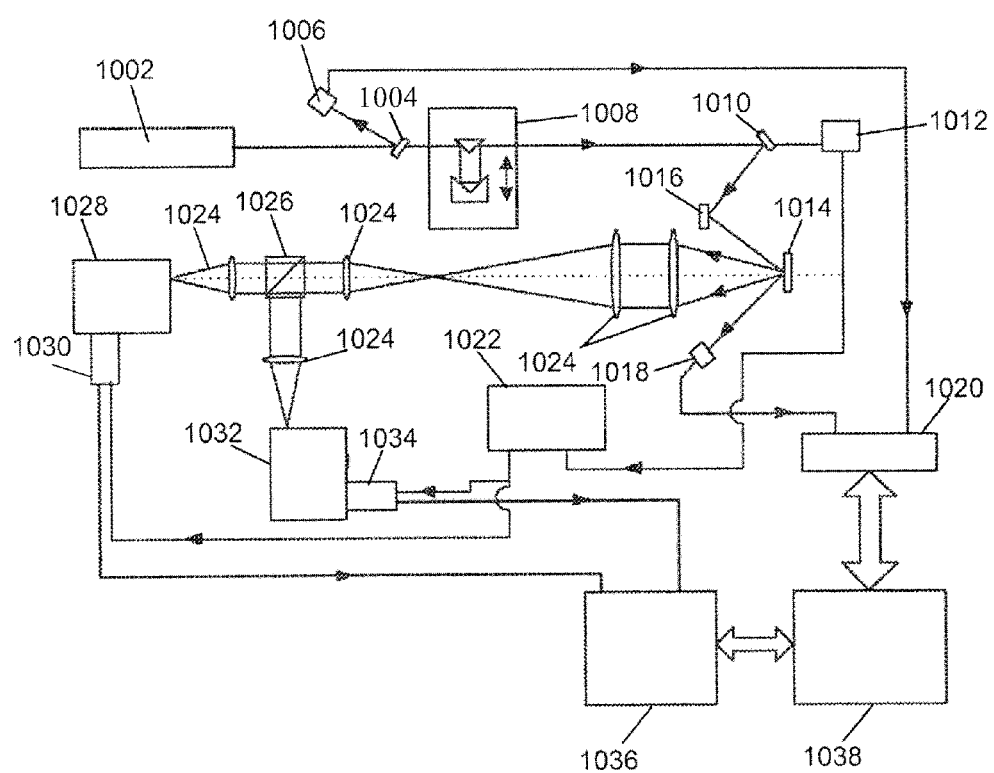
FIG. 16 depicts a third example of an apparatus for inspection of an object according to an embodiment of the present invention.

FIG. 16 illustrates a third example set up, again for the purposes of illustration. This is a variation of the set up shown in FIG. 15.

FIG. 16 illustrates a system for detection of contamination on the surface of semiconductors/metals. The optical system (shown in general as reference numeral 706 in FIG. 7) includes: a picosecond laser 1002, a beam splitter 1004, photon counter 1006, optical delay line 1008, beam splitter 1010, fast p-i-n photodiode 1012, sample on a holder 1014, mirror 1016, photon counter 1018, autocorrelator unit 1020, digital delay generator 1022, secondary emission condensing optical unit (including lenses 1024 and achromatic beam splitter 1026), two spectrometers 1028, 1032 each equipped with EDCCD (Electron Multiplying Charge Coupled Device) gated image detectors 1030, 1034, time correlated Spectroanalyzer Unit 1036 and a computer 1038.

In operation, the laser beam passing via optical delay line 1008 comes to sample 1014 and reflects. Using photon counters 1006 and 1018 and autocorrelator unit 1020, the autocorrelation function of the laser beam is measured. Secondary spontaneous emission (photoluminescence and scattered light) from contamination is condensed and directed to optical spectrometers 1028, 1032, equipped with gated EMCCD units 1030, 1034. Detection of the secondary emission process is separated on laser emission temporary and spectrally. Thus, "noise" i.e. strain light of the laser source, will be neglected.

The secondary radiation signal is detected by spectrometers 1028, 1032 and delayed in time with respect to the laser pulse. Fluctuation of this signal that has a distribution different than the laser indicates presence of contamination on the sample surface. The fluctuation comparison is done on the basis of correlation analysis of signals. Digital delay generator 1022 receives a strobe signal from photodiode 1012 and outputs a strobe signal to EMCCD 1030 and a strobe+t signal to EMCCD 1034. Autocorrelator unit 1020 receives a stop signal from photon counter 1018.

Figure 17:
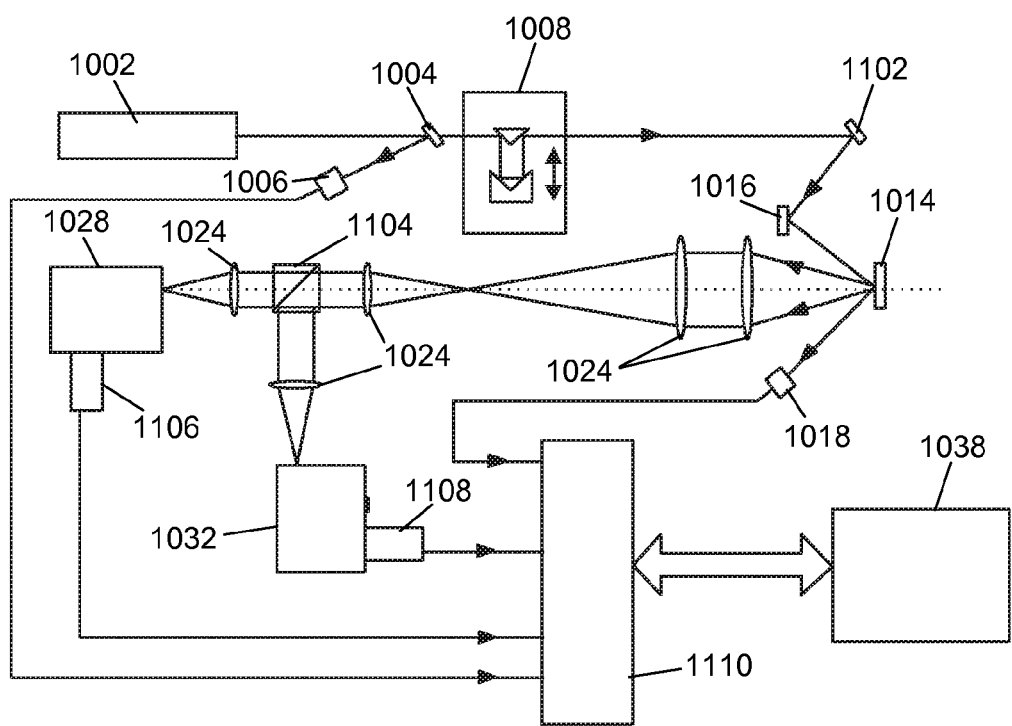
FIG. 17 depicts a fourth example of an apparatus for inspection of an object according to an embodiment of the present invention.

FIG. 17 illustrates a fourth example set-up, again for the purposes of illustration. This is a variation of the set-up shown in FIG. 16. Similar elements are illustrated with similar reference numerals and function in the same manner as mentioned above. They will therefore not be described again in detail.

FIG. 17 illustrates a system for detection of contamination on the surface of semiconductors/metals. The optical system (shown in general as reference numeral 706 in FIG. 7) includes mirror 1102 in place of beam splitter 1010 in FIG. 16 and polarizing beam splitter 1104 in place of achromatic beam splitter 1026 in FIG. 16. The two spectrometers 1028, 1032 are each equipped with photon counters 1106, 1108 respectively.

In operation, the laser beam passing via optical delay 1008 line comes to sample 1014 and reflects. Secondary spontaneous emission (photoluminescence and scattered light) from contamination is condensed and directed to optical spectrometers 1028, 1032, equipped with photon counters 1106, 1108. The correlator unit 1110 receives a laser stop signal from photon counter 1018, stop/start signals from photon counters 1106, 1108 and a laser start signal from photon counter 1006.

Embodiments of the present invention provide several advantages. The time resolved spectroscopy of secondary photon emission from various type of particle contaminants allows an improvement in the capability to detect particles. Even if a particle exhibits a similar magnitude photoluminescence response to that of an object being inspected, the analysis of the time resolved spectrum provides a way to distinguish this particle from that of the object. For particles which exhibit different magnitude photoluminescence responses to that of the object being inspected, the time resolved spectroscopy yields additional accuracy in the detection.

Furthermore, when time and energy resolved spectroscopy techniques are combined, the range of particles that can be discriminated from the object to be inspected is increased. Even if a particle exhibits a similar response to that of the object in either of the time or energy resolved domains, it is unlikely to exhibit the same response as the object in the other of the time or energy resolved domains. If an energy resolved spectroscopy is carried out first, the results can be used to identify signals of interest, to which time resolved spectroscopy can be applied. Equally, if a time resolved spectroscopy is carried out first, the results can be used to identify signals of interest to which energy resolved spectroscopy can be applied.

Embodiments of the methods and apparatus of the disclosure also allow the detection of a particle on a patterned reticle without the necessity of resolving the pattern itself and without comparing the signal to a reference signal. This allows the inspection of "single die" reticles because a complicated die-to-database inspection is not required.

In addition, avoiding comparison of two reference objects avoids the associated image alignment issues.

Embodiments of the methods and apparatus of the present disclosure can in principle be used for the inspection of any type of pattern or mask. The method can also be used to detect smaller particles which are, for example, less than 100 nanometers, less than 50 nanometers or even less than 20 nanometers, and can be used for detection of all these on the patterned side of substrates such as EUV reticles.

Another advantage compared with conventional (scattering-based) detection systems is that the signal is "emitted" by the particle and not "scattered". Light scattered by a particle of radius R scales much as $\sim R^6$, so as the particle gets smaller, it becomes much more difficult to detect it. In the technique of this disclosure the signal comes from secondary "emission" which scales differently: for organic PL as $\sim R^3$, for metal oxides the impurities are detected (so also $\sim R^3$). For metal particles adsorbed molecules on the surface are detected (so theoretically as $\sim R^2$). However, again this type of detection, since it is wavelength and/or time resolved, can achieve very good Signal-to-Noise ratio, so single molecules and/or atoms can be detected, extending the sensitivity to extremely small particles, for example those around or less than 20 nm in size.

The inspection time can also be very fast, for example it can be under fifteen minutes.

Furthermore, the use of the correlation techniques described above can help distinguish the particle spectra from that of noise caused by molecular carbon contamination on the surface.

It will also be appreciated that the embodiments described above can be used with reflective objects/reticles, or with transmissive objects/reticles.

Figure 18:
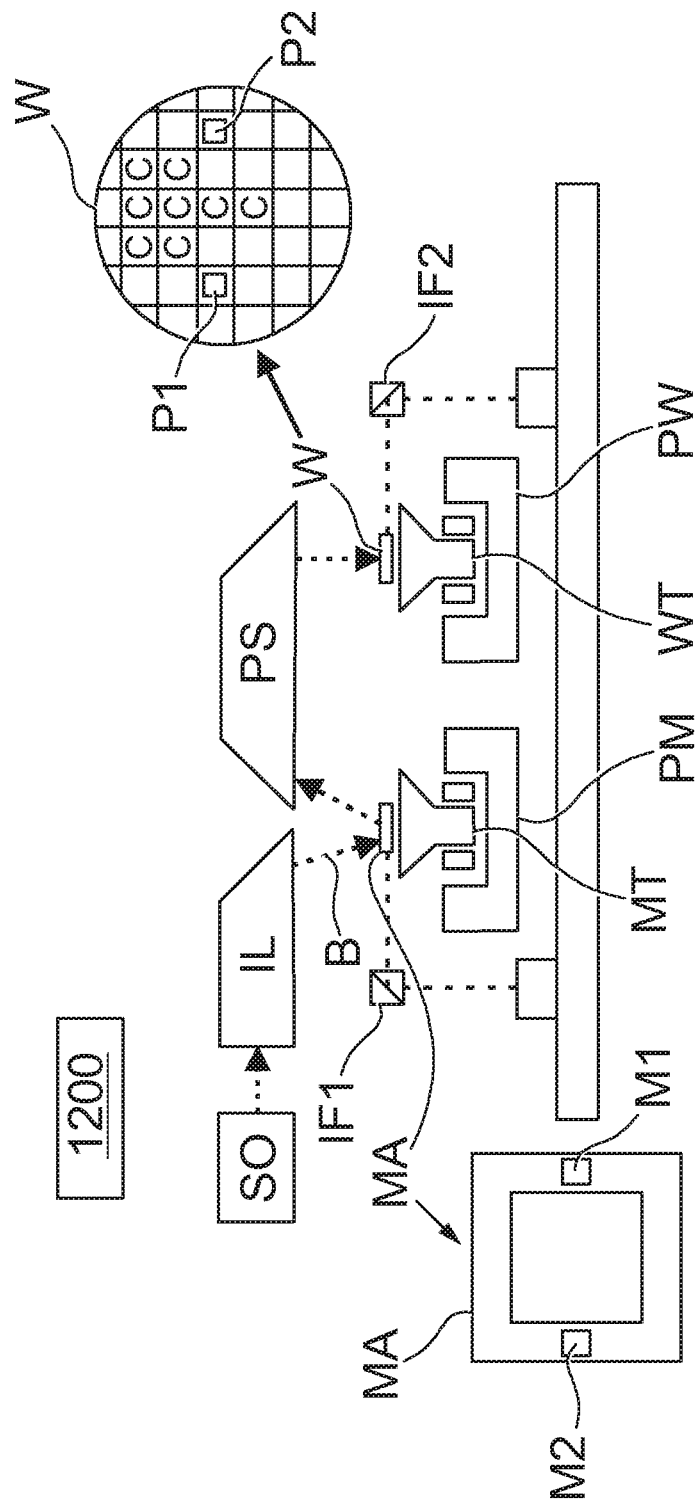
FIG. 18 depicts a reflective lithographic apparatus according to an embodiment of the present invention.
Figure 19:
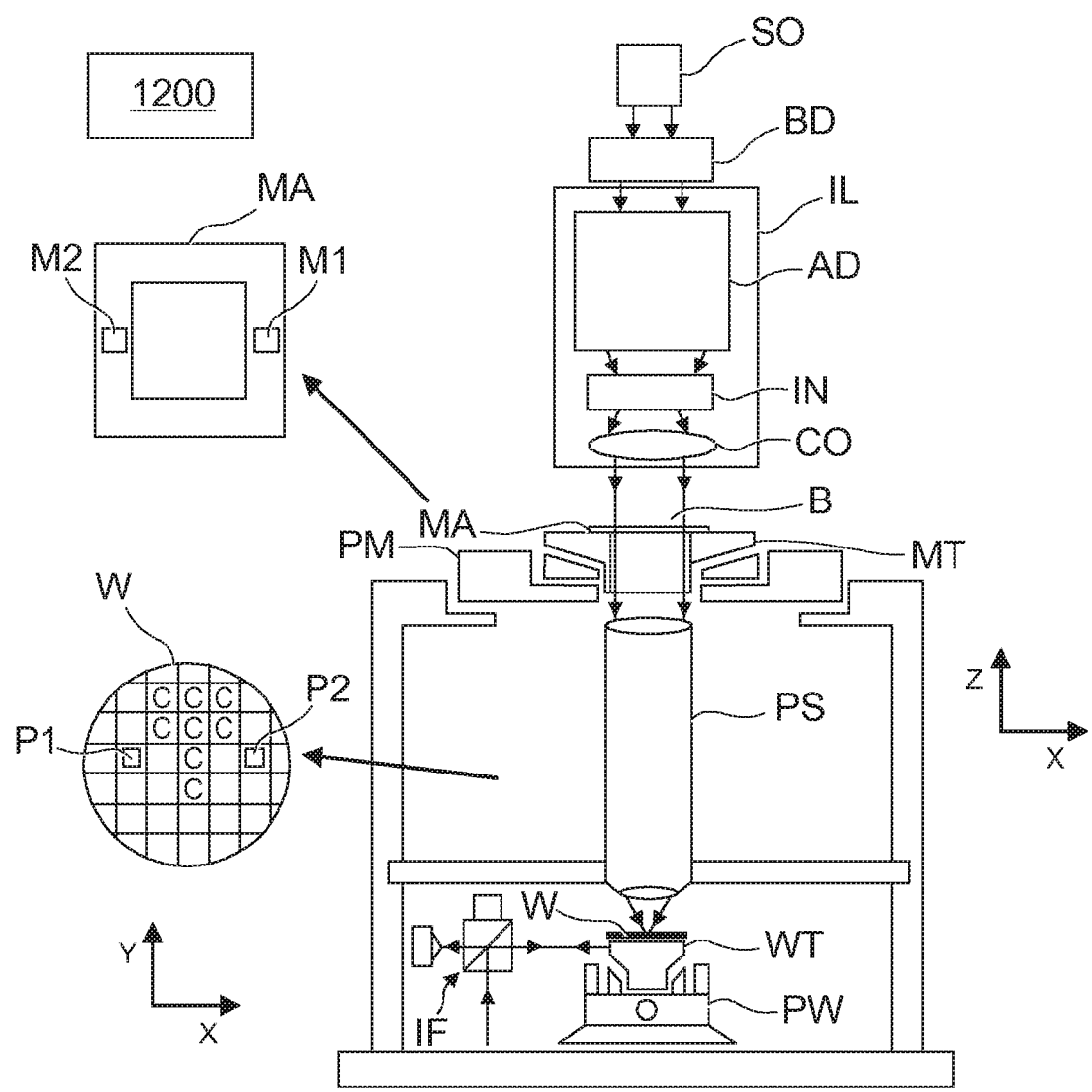
FIG. 19 depicts a transmissive lithographic apparatus according to an embodiment of the present invention.
Figure 20:
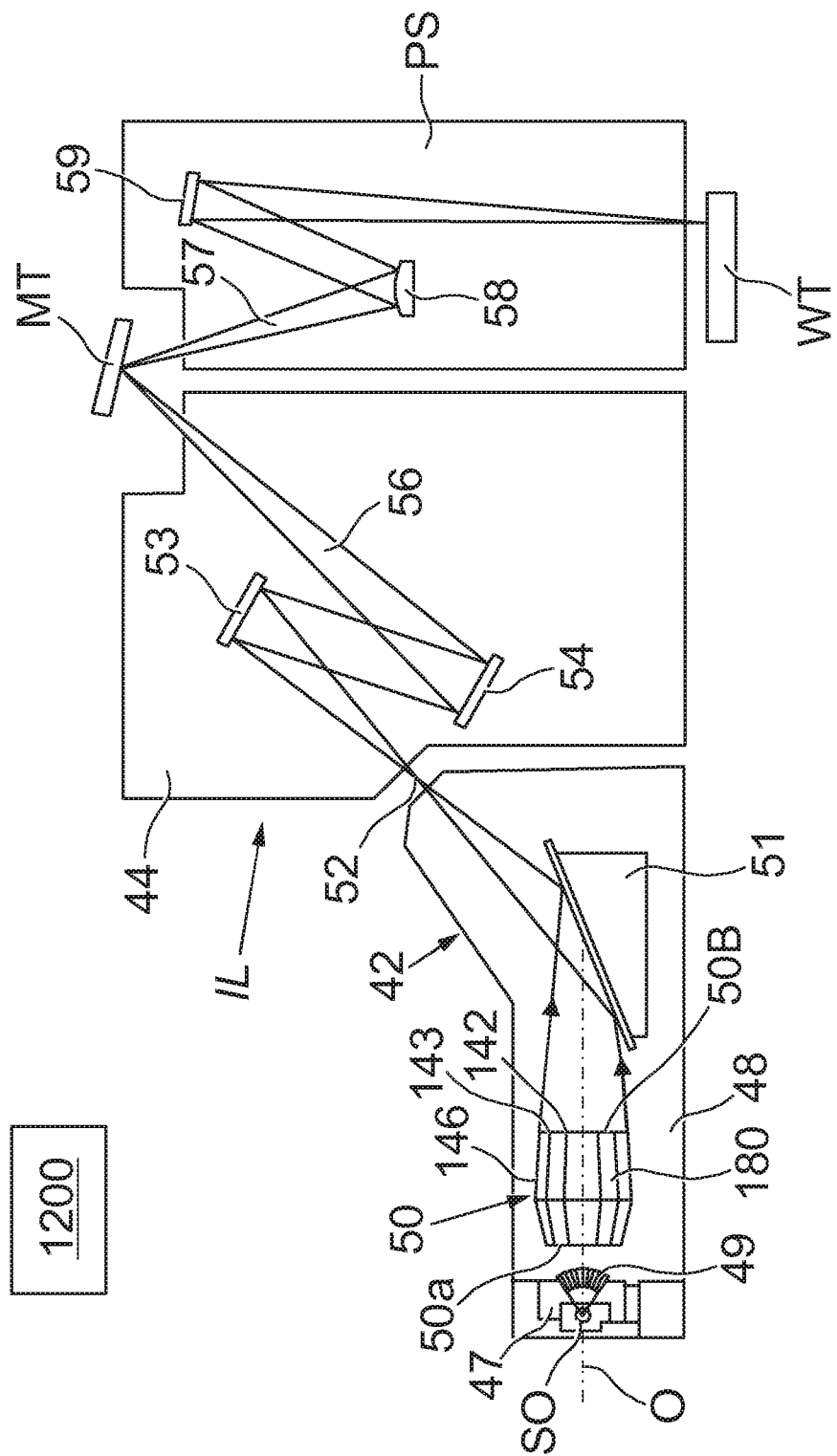
FIG. 20 depicts an example EUV lithographic apparatus according to an embodiment of the present invention.

The embodiments described above are depicted as separate devices. Alternatively, they may optionally be provided as an in-tool device, that is, within a lithographic system. As a separate apparatus, it can be used for purposes of reticle inspection (e.g., prior to shipping). As an in-tool device, it can perform a quick inspection of a reticle prior to using the reticle for a lithographic process. FIGS. 18 to 20 illustrate examples of lithographic systems that can incorporate reticle inspection system 1200 as an in-tool device. In FIGS. 18 to 20, reticle inspection system 1200 is shown together with the respective lithography system. The reticle inspection system 1200 can be the object inspection system of any of the embodiments illustrated in FIGS. 1 to 17, or variations thereof.

The following description presents detailed example environments in which embodiments of the present invention may be implemented.

FIG. 18 schematically depicts a lithographic apparatus according to one embodiment of the invention. The apparatus includes:
- an illumination system (illuminator) IL that receives a radiation beam from a radiation source SO, and which is configured to condition a radiation beam B (e.g. EUV radiation).
- a support structure (e.g. a mask table) MT constructed to support a patterning device (e.g. a mask or a reticle) MA and connected to a first positioner PM configured to accurately position the patterning device MA;
- a substrate table (e.g. a wafer table) WT constructed to hold a substrate (e.g. a resist coated wafer) W and connected to a second positioner PW configured to accurately position the substrate WT; and
- a projection system (e.g. a reflective projection lens system) PS configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structures MT and WT hold objects, including a patterning device MA and support structure WT respectively. Each support structure MT, WT holds its respective object MA, W in a manner that depends on the orientation of the object MA, W, the design of the lithographic apparatus, and other conditions, such as for example whether or not the object MA, W is held in a vacuum environment. The or each of the support structures MT, WT can use mechanical, vacuum, electrostatic or other clamping techniques to hold the objects MA, W. The support structures MT, WT may include a frame or a table, for example, which may be fixed or movable as required. The support structures MT, WT may ensure that the respective objects MA, W are at a desired position, for example with respect to the projection system PS.

With the aid of the second positioner PW and position sensor IF2 (e.g., an interferometric device, linear encoder or capacitive sensor), the substrate table WT may be moved accurately, e.g. so as to position different target portions C in the path of the radiation beam B. Similarly, the first positioner PM and another position sensor IF1 may be used to accurately position the patterning device (e.g., mask) MA with respect to the path of the radiation beam B. Patterning device (e.g., mask) MA and substrate W may be aligned using mask alignment marks M1, M2 and substrate alignment marks P1, P2.

The term "patterning device" should be broadly interpreted as referring to any device that can be used to impart a radiation beam with a pattern in its cross-section such as to create a pattern in a target portion of the substrate. The pattern imparted to the radiation beam may correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" may encompass any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. It may be desired to use a vacuum for EUV or electron beam radiation since other gases may absorb too much radiation or electrons. A vacuum environment may therefore be provided to the whole beam path with the aid of a vacuum wall and vacuum pumps.

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

As depicted in FIG. 18, the apparatus is of a reflective type (e.g. employing a reflective mask). Alternatively, the apparatus may be of a transmissive type (e.g. employing a transmissive mask). A transmissive type apparatus is shown in FIG. 13.

Referring to FIG. 19, the illuminator IL receives a radiation beam from a radiation source SO. The source and the lithographic apparatus may be separate entities, for example when the source SO is an excimer laser. In such cases, the source SO is not considered to form part of the lithographic apparatus and the radiation beam is passed from the source SO to the illuminator IL with the aid of a beam delivery system BD including, for example, suitable directing mirrors and/or a beam expander. In other cases the source SO may be an integral part of the lithographic apparatus, for example when the source SO is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator IL may be used to condition the radiation beam, to have a desired uniformity and intensity distribution in its cross section.

The radiation beam B is incident on the patterning device (e.g., mask) MA, which is held on the support structure (e.g., mask table) MT, and is patterned by the patterning device. After traversing the patterning device (e.g. mask) MA, the radiation beam B passes through the projection system PS, which focuses the beam onto a target portion C of the substrate W. With the aid of the second positioner PW and position sensor IF2 (e.g. an interferometric device, linear encoder or capacitive sensor), the substrate table WT can be moved accurately, e.g. so as to position different target portions C in the path of the radiation beam B. Similarly, the first positioner PM and another position sensor (not shown) can be used to accurately position the patterning device (e.g. mask) MA with respect to the path of the radiation beam B. Patterning device (e.g. mask) MA and substrate W may be aligned using mask alignment marks M1, M2 and substrate alignment marks P1, P2.

FIG. 19 also illustrates a number of other components used in a transmissive type lithographic apparatus, the form and operation of which will be familiar to a skilled artisan.

The depicted apparatus of both FIGS. 18 and 19 could be used in at least one of the following modes:

1. In step mode, the support structure (e.g. mask table) MT and the substrate table WT are kept essentially stationary, while an entire pattern imparted, to the radiation beam is projected onto a target portion C at one time (i.e. a single static exposure). The substrate table WT is then shifted in the X and/or Y direction so that a different target portion C can be exposed.

2. In scan mode, the support structure (e.g. mask table) MT and the substrate table WT are scanned synchronously while a pattern imparted to the radiation beam is projected onto a target portion C (i.e. a single dynamic exposure). The velocity and direction of the substrate table WT relative to the support structure (e.g. mask table) MT may be determined by the (de-)magnification and image reversal characteristics of the projection system PS.

3. In another mode, the support structure (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

FIG. 20 shows the apparatus of FIG. 18 in more detail, including a radiation system 42, the illumination system IL, and the projection system PS. The radiation system 42 includes the radiation source SO which may be formed by a discharge plasma. EUV radiation may be produced by a gas or vapor, for example Xe gas, Li vapor or Sn vapor in which a very hot plasma is created to emit radiation in the EUV range of the electromagnetic spectrum. The very hot plasma is created by causing an at least partially ionized plasma by, for example, an electrical discharge. Partial pressures of, for example, 10 Pa of Xe, Li, Sn vapor or any other suitable gas or vapor may be required for efficient generation of the radiation. In an embodiment, a Sn source is applied as an EUV source. The radiation emitted by radiation source SO is passed from a source chamber 47 into a collector chamber 48 via an optional gas barrier or contaminant trap 49 (in some cases also referred to as contaminant barrier or foil trap) which is positioned in or behind an opening in source chamber 47. The contaminant trap 49 may include a channel structure. Contamination trap 49 may also include a gas barrier or a combination of a gas barrier and a channel structure. The contaminant trap or contaminant barrier 49 further indicated herein at least includes a channel structure, as known in the art.

The collector chamber 48 may include a radiation collector 50 which may be a grazing incidence collector (including so-called grazing incidence reflectors). Radiation collector 50 has an upstream radiation collector side 50a and a downstream radiation collector side 50b. Radiation passed by collector 50 can be reflected off a grating spectral filter 51 to be focused in an intermediate focus point 52 at an aperture in the collector chamber 48. The beam of radiation emanating from collector chamber 48 traverses the illumination system IL via so-called normal incidence reflectors 53, 54, as indicated in FIG. 20 by the radiation beam 56. The normal incidence reflectors direct the beam 56 onto a patterning device (e.g. reticle or mask) positioned on a support (e.g. reticle or mask table) MT. A patterned beam 57 is formed, which is imaged by projection system PS via reflective elements 58, 59 onto a substrate carried by wafer stage or substrate table WT. More elements than shown may generally be present in illumination system IL and projection system PS. Grating spectral filter 51 may optionally be present, depending upon the type of lithographic apparatus. Further, there may be more mirrors present than those shown in the Figures, for example there may be 1-4 more reflective elements present than the elements 58, 59 shown in FIG. 20. Radiation collectors similar to radiation collector 50 are known from the art.

Radiation collector 50, is described herein as a nested collector with reflectors 142, 143, and 146. The nested radiation collector 50, as schematically depicted in FIG. 20, is herein further used as an example of a grazing incidence collector (or grazing incidence collector mirror). However, instead of a radiation collector 50 including a grazing incidence mirror, a radiation collector including a normal incidence collector may be applied. Hence, where applicable, collector mirror 50 as grazing incidence collector may also be interpreted as collector in general and in a specific embodiment also as normal incidence collector.

Further, instead of a grating 51, as schematically depicted in FIG. 20, also a transmissive optical filter may be applied.

Optical filters transmissive for EUV and less transmissive for or even substantially absorbing UV radiation are known in the art. Hence, "grating spectral purity filter" is herein further indicated as "spectral purity filter" which includes gratings or transmissive filters. Not depicted in schematic FIG. 20, but also included as optional optical elements may be EUV transmissive optical filters, for instance arranged upstream of collector mirror 50, or optical EUV transmissive filters in illumination system IL and/or projection system. PS.

The radiation collector 50 is usually placed in the vicinity of the source SO or an image of the source SO. Each reflector 142, 143, 146 may include at least two adjacent reflecting surfaces, the reflecting surfaces further from the source SO being placed at smaller angles to the optical axis O than the reflecting surface that is closer to the source SO. In this way, a grazing incidence collector 50 is configured to generate a beam of (E)UV radiation propagating along the optical axis O. At least two reflectors may be placed substantially coaxially and extend substantially rotationally symmetric about the optical axis O. It should be appreciated that radiation collector 50 may have further features on the external surface of outer reflector 146 or further features around outer reflector 146. For example, a further feature may be a protective holder, or a heater. Reference number 180 indicates a space between two reflectors, e.g. between reflectors 142 and 143.

During use, on one or more of the outer reflectors 146 and inner reflectors 142 and 143 deposition may be found. The radiation collector 50 may be deteriorated by such deposition (deterioration by debris, e.g. ions, electrons, clusters, droplets, electrode corrosion from the source SO). Deposition of Sn, for example due to a Sn source, may, after a few monolayers, be detrimental to reflection of the radiation collector 50 or other optical elements, which may necessitate the cleaning of such optical elements.

Although specific reference may be made in this text to the use of lithographic apparatus in the manufacture of ICs, it should be understood that the lithographic apparatus described herein may have other applications, such as, the manufacture of integrated optical systems, guidance and detection patterns for magnetic domain memories, flat-panel displays, liquid-crystal displays (LCDs), thin film magnetic heads, etc.

Although specific reference may have been made above to the use of embodiments of the invention in the context of optical lithography, it will be appreciated that the invention may be used in other applications, for example imprint lithography, and where the context allows, is not limited to optical lithography.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

It is also to be appreciated that in the embodiments above, an optical path length difference between a first optical path from the illumination source to the detector and a second optical path from the illumination source to the detector should be less than a coherence length of the illumination source. An optical path (or optical path length) is a product of geometrical length (s) and refractive index (n) as shown in the following equation: $OPL = c \int n(s) ds$, where integration is along a ray. In an example case of straight rays in two branches (from the light source to the detector) with uniform mediums, the optical path difference (OPD) is equal to $(n1*s1)-(n2*s2)$.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below. It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents. Other aspects of the invention are set out as in the following numbered clauses:

1. A method for inspection of an object comprising:
    illuminating the object with a radiation beam,
    analyzing secondary photon emissions from the object with time resolved spectroscopy, and
    determining that a particle is present if a time resolved spectroscopic signal is detected which is different from a signal that would be emitted by the object in the absence of a particle.
2. The method of clause 1, wherein the step of analyzing secondary photon emissions from the object with time resolved spectroscopy comprises recording a photoluminescence signal.
3. The method of clause 1 or clause 2, wherein the inspected object comprises a patterning device.
4. The method of clause 3, wherein the patterning device is a reticle or an EUV reticle.
5. The method of any preceding clause, further comprising the step of analyzing secondary photon emissions from the object with energy resolved spectroscopic analysis.

6. The method of any preceding clause, used to determine the presence of metal, metal oxide, or organic particles on the surface of the object.
7. The method of any preceding clause, further comprising a noise reduction technique.
8. The method of clause 7, where said noise reduction technique comprises a correlation technique to remove noise from the emitted spectra.
9. The method of clause 7, where said noise reduction technique comprises chaos theory methods.
10. The method of any preceding clause, wherein illuminating the object with a radiation beam comprises illuminating said object at normal incidence.
11. The method of clause 10, wherein radiation is collected with a Schwarzschild type collector.
12. The method of any of clauses 1 to 9, wherein illuminating the object with a radiation beam comprises providing off-axis illumination from a more than one direction.
13. The method of clause 12, wherein said off-axis illumination is provided from four different directions.
14. The method of clause 12 or clause 13, wherein said off-axis illumination is provided as an annular radiation beam.
15. The method of any of clauses 12 to 14, wherein illuminating the object with a radiation beam comprises splitting said radiation beam into a plurality of split beams, each of which is incident upon the object at different a different angle to the other split beams.
16. The method of any preceding clause, performed over a first area of said object; and repeated for sub-portions of said first area if a particle is detected.
17. The method of clause 16, comprising performing further repetitions until a desired spatial resolution limit is reached.
18. Apparatus for inspection of an object, comprising a radiation source arranged to emit a radiation beam onto the object and a spectrometer arranged to analyze secondary photon emissions from the object with time resolved spectroscopy and to determine that a particle is present if a time resolved spectroscopic signal is detected which is different from a signal that would be emitted by the object in the absence of a particle.
19. The apparatus of clause 18, wherein the spectrometer is arranged to analyze time resolved spectroscopy in respect of a photoluminescence signal.
20. The apparatus of clause 18 or clause 19, wherein the inspected object comprises a patterning device.
21. The apparatus of clause 20, wherein the patterning device is a reticle or an EUV reticle.
22. The apparatus of any of clauses 18 to 21, wherein the wherein the spectrometer is further arranged to analyze secondary photon emissions from the object with time resolved spectroscopy.
23. The apparatus of any of clauses 18 to 22, further comprising a noise reduction module.
24. The apparatus of clause 23, where said noise reduction module comprises a correlator.
25. The apparatus of clause 23, where said noise reduction module comprises chaos theory module.
26. The apparatus of any of clauses 18 to 25, wherein said radiation source is arranged to illuminate the object with a radiation beam at normal incidence.
27. The apparatus of clause 26, comprising a Schwarzschild type collector for collecting radiation.
28. The apparatus of any of clauses 18 to 25, comprising means to direct radiation onto the object from a more than one direction.
29. The apparatus of clause 28, wherein said off-axis illumination is provided from four different directions.
30. The apparatus of clause 28 or clause 29, wherein said off-axis illumination is provided as an annular radiation beam.
31. The apparatus of any of clauses 28 to 30, comprising one or more beamsplitters for splitting said radiation beam into a plurality of split beams, each of which is incident upon the object at different a different angle to the other split beams.
32. The apparatus of any of clauses 18 to 31, comprising control means to perform a detection over a first area of said object; and then to repeat the detection for sub-portions of said first area if a particle is detected.
33. The apparatus of clause 32, wherein the control means is adapted to perform further repetitions until a desired spatial resolution limit is reached.
34. A lithographic apparatus comprising apparatus for inspection of an object comprising a radiation source arranged to emit a radiation beam onto the object and a spectrometer arranged to analyze secondary photon emissions from the object with time resolved spectroscopy and to determine that a particle is present if a time resolved spectroscopic signal is detected which is different from a signal that would be emitted by the object.
35. A computer program product comprising instructions that, when executed upon a computer enable it to carry out a data analysis method for use in the method of any of clauses 1 to 17.
36. A method for inspection of an object, comprising:
    illuminating the object with a radiation beam,
    analyzing secondary photon emissions from the object with time resolved spectroscopy, and
    determining that a particle is present if a time resolved spectroscopic signal is detected which is different from a signal that would be emitted by the object in the absence of a particle.
37. The method of clause 36, wherein the step of analyzing secondary photon emissions from the object with time resolved spectroscopy comprises recording a photoluminescence signal.
38. The method of clause 36, wherein the inspected object comprises a patterning device.
39. The method of clause 38, wherein the patterning device is a reticle or an EUV reticle.
40. The method of clause 36, further comprising the step of analyzing secondary photon emissions from the object with energy resolved spectroscopic analysis.
41. The method of clause 36, wherein the determining step determines the presence of metal, metal oxide, or organic particles on the surface of the object.
42. The method of clause 36, further comprising reducing noise according to a noise reduction technique.
43. The method of clause 42, where the noise reduction technique comprises a correlation technique to remove noise from the emitted spectra.
44. The method of clause 42, where the noise reduction technique comprises a chaos theory method.
45. The method of clause 36, wherein illuminating the object with a radiation beam comprises illuminating said object at normal incidence.
46. The method of clause 45, wherein radiation is collected with a Schwarzschild type collector.
47. The method of clause 36, wherein illuminating the object with a radiation beam comprises providing off-axis illumination from a more than one direction.

48. The method of clause 47, wherein said off-axis illumination is provided from four different directions.
49. The method of clause 48, wherein said off-axis illumination is provided as an annular radiation beam.
50. The method of clause 47, wherein illuminating the object with a radiation beam comprises splitting said radiation beam into a plurality of split beams, each of which is incident upon the object at different a different angle to the other split beams.
51. The method of clause 36, performed over a first area of said object; and repeated for sub-portions of said first area if a particle is detected.
52. The method of clause 51, comprising performing further repetitions until a desired spatial resolution limit is reached.
53. An apparatus for inspection of an object, comprising:
    a radiation source arranged to emit a radiation beam onto the object; and
    a spectrometer arranged to analyze secondary photon emissions from the object with time resolved spectroscopy and to determine that a particle is present if a time resolved spectroscopic signal is detected which is different from a signal that would be emitted by the object in the absence of a particle.
54. The apparatus of clause 53, wherein the spectrometer is arranged to analyze time resolved spectroscopy in respect of a photoluminescence signal.
55. The apparatus of clause 53, wherein the inspected object comprises a patterning device.
56. The apparatus of clause 55, wherein the patterning device is a reticle or an EUV reticle.
57. The apparatus of clause 53, wherein the wherein the spectrometer is further arranged to analyze secondary photon emissions from the object with time resolved spectroscopy.
58. The apparatus of clause 53, further comprising a noise reduction module.
59. The apparatus of clause 58, where the noise reduction module comprises a correlator.
60. The apparatus of clause 58, where the noise reduction module comprises a chaos theory module.
61. The apparatus of any clause 53, wherein said radiation source is arranged to illuminate the object with a radiation beam at normal incidence.
62. The apparatus of clause 61, comprising a Schwarzschild type collector for collecting radiation.
63. The apparatus of clause 53, comprising means to direct radiation onto the object from a more than one direction.
64. The apparatus of clause 63, wherein said off-axis illumination is provided from four different directions.
65. The apparatus of clause 63, wherein said off-axis illumination is provided as an annular radiation beam.
66. The apparatus of clause 63, comprising one or more beamsplitters for splitting said radiation beam into a plurality of split beams, each of which is incident upon the object at different a different angle to the other split beams.
67. The apparatus of clause 53, comprising control means to perform a detection over a first area of said object; and then to repeat the detection for sub-portions of said first area if a particle is detected.
68. The apparatus of clause 67, wherein the control means is adapted to perform further repetitions until a desired spatial resolution limit is reached.
69. A lithographic apparatus comprising:
    an apparatus for inspection of an object, comprising:
        a radiation source arranged to emit a radiation beam onto the object; and
        a spectrometer arranged to analyze secondary photon emissions from the object with time resolved spectroscopy and to determine that a particle is present if a time resolved spectroscopic signal is detected which is different from a signal that would be emitted by the object.
70. A computer readable medium having stored thereon computer-executable instructions that, if executed by a computer, cause the computer to perform a data analysis method comprising:
    illuminating an object with a radiation beam,
    analyzing secondary photon emissions from the object with time resolved spectroscopy, and
    determining that a particle is present if a time resolved spectroscopic signal is detected which is different from a signal that would be emitted by the object in the absence of a particle.

What is claimed is:

1. A method for inspection of an object, comprising:
    illuminating a surface of an object with a radiation beam;
    analyzing secondary photon emissions from the surface of the object with time resolved spectroscopy, wherein the analyzing comprises:
        analyzing a first portion of the secondary photon emissions received through a first optical path,
        analyzing a second portion of the secondary photon emissions received through a second optical path, wherein the first and second portions of the secondary photon emissions comprise wavelengths that are the same, and
        performing a correlation between the analysis of the first portion and the analysis of the second portion; and
    determining that a particle disposed on the surface of the object is present if the correlation indicates secondary photon emissions,
    wherein said illuminating the object with a radiation beam comprises providing off-axis illumination from more than one direction.
2. The method of claim 1, wherein said off-axis illumination is provided from four different directions.
3. The method of claim 1, wherein said off-axis illumination is provided as an annular radiation beam.
4. The method of claim 1, wherein illuminating the surface of the object with a radiation beam comprises splitting said radiation beam into a plurality of split beams, each of which is incident upon the surface of the object at a different angle to the other split beams.
5. The method of claim 1, wherein the analyzing secondary photon emissions from the surface of the object with time resolved spectroscopy further comprises recording a photoluminescence signal.
6. The method of claim 1, wherein the inspected object comprises a patterning device, said patterning device being a reticle or an extreme ultraviolet (EUV) reticle.
7. The method of claim 1, further comprising analyzing secondary photon emissions from the surface of the object with energy resolved spectroscopic analysis.
8. The method of claim 1, wherein the determining further comprises determining that the particle comprises metal, metal oxide, or organic material based on the time-resolved spectroscopic signal.
9. The method of claim 1, wherein the method is performed over a first area of said surface of the object, and then repeated for sub-portions of said first area if a particle is detected.
10. The method of claim 9, further comprising performing further repetitions until a desired spatial resolution limit is reached.

11. An Apparatus for inspection of a surface of an object, comprising;
 a radiation source configured to emit a radiation beam onto the surface of the object;
 a spectrometer module configured to:
  analyze a first portion of secondary photon emissions received through a first optical path from the surface of the object with time resolved spectroscopy,
  analyze a second portion of secondary photon emissions received through a second optical path, wherein the first and second portions of the secondary photon emissions comprise wavelengths that are the same,
  perform a correlation between the analysis of the first portion and the analysis of the second portion, and
  determine that a particle disposed on the surface of the object is present if the correlation indicates secondary photon emissions; and
 one or more optical elements configured to direct radiation onto the surface of the object from more than one direction.

12. The apparatus of claim 11, wherein the one or more optical elements comprise one or more beamsplitters configured to split said radiation beam into a plurality of split beams, each of which is incident upon the object at a different angle to the other split beams.

13. The apparatus of claim 11, comprising a controller configured to perform a detection over a first area of said surface of the object, and then to repeat the detection for sub-portions of said first area if a particle is detected.

14. A lithographic apparatus for inspection of a surface of an object, comprising:
 a radiation source configured to emit a radiation beam onto the surface of the object;
 a spectrometer configured to:
  analyze a first portion of secondary photon emissions received through a first optical path from the surface of the object with time resolved spectroscopy,
  analyze a second portion of secondary photon emissions received through a second optical path, wherein the first and second portions of the secondary photon emissions comprise wavelengths that are the same,
  perform a correlation between the analysis of the first portion and the analysis of the second portion, and
  determine that a particle disposed on the surface of the object is present if the correlation indicates secondary photon emissions; and
 one or more optical elements configured to direct radiation onto the surface of the object from more than one direction.

* * * * *